(12) United States Patent
Boyden et al.

(10) Patent No.: US 12,233,184 B2
(45) Date of Patent: Feb. 25, 2025

(54) DIMETHYLACRYLAMIDE (DMAA) HYDROGEL FOR EXPANSION MICROSCOPY (ExM)

(71) Applicant: Massachusetts Institute of Technology, Cambridge, MA (US)

(72) Inventors: Edward Stuart Boyden, Chestnut Hill, MA (US); Nikita Obidin, Somerville, MA (US); Ruixuan Gao, Cambridge, MA (US); Linyi Gao, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 767 days.

(21) Appl. No.: 17/144,551

(22) Filed: Jan. 8, 2021

(65) Prior Publication Data
US 2021/0196856 A1 Jul. 1, 2021

Related U.S. Application Data

(63) Continuation of application No. PCT/US2018/041930, filed on Jul. 13, 2018.

(51) Int. Cl.
*B01L 3/00* (2006.01)
*A61L 27/16* (2006.01)
(Continued)

(52) U.S. Cl.
CPC .............. *A61L 27/16* (2013.01); *A61L 27/56* (2013.01); *C08F 220/56* (2013.01); *C08L 33/26* (2013.01); *G01N 1/312* (2013.01)

(58) Field of Classification Search
CPC ........ A61L 27/16; A61L 27/56; C08F 220/56; C08L 33/26; G01N 1/312
See application file for complete search history.

(56) References Cited

U.S. PATENT DOCUMENTS 5,840,862 A    11/1998  Bensimon et al.
5,952,232 A     9/1999  Rothman
(Continued)

FOREIGN PATENT DOCUMENTS

CN    104350372 A    2/2015
CN    111848855 A   10/2020
(Continued)

OTHER PUBLICATIONS

Asano, S. M. et al., "Expansion Microscopy: Protocols for Imaging Proteins and RNA in Cells and Tissues", Current Protocols in Cell Bio., vol. 80, No. 1, Online: DOI: 10.1002/cpcb.56. Retrieved from the Internet: URL:https://onlinelibrary.wiley.com/doi/full-xml/10.1002/cpcb.56> [retrieved on Feb, 26, 2021], Sept. 2, 2018, p. 41.
(Continued)

*Primary Examiner* — Jennifer Wecker
*Assistant Examiner* — Oyeleye Alexander Alabi
(74) *Attorney, Agent, or Firm* — Pierce Atwood LLP

(57) ABSTRACT

The invention provides a method for preparing an expanded cell or tissue sample suitable for microscopic analysis. Expanding the sample can be achieved by binding, e.g., anchoring, key biomolecules to a DMAA-TF polymer network and swelling, or expanding, the polymer network, thereby moving the biomolecules apart as further described herein. As the biomolecules are anchored to the polymer network isotropic expansion of the polymer network retains the spatial orientation of the biomolecules resulting in an expanded, or enlarged, sample.

28 Claims, 4 Drawing Sheets

(51) Int. Cl.

| | |
|---|---|
| *A61L 27/56* | (2006.01) |
| *B01F 23/00* | (2022.01) |
| *B01F 23/41* | (2022.01) |
| *B01F 101/23* | (2022.01) |
| *B01L 9/00* | (2006.01) |
| *B23Q 17/24* | (2006.01) |
| *C07K 14/705* | (2006.01) |
| *C08F 220/56* | (2006.01) |
| *C08L 33/26* | (2006.01) |
| *C12M 1/34* | (2006.01) |
| *C12Q 1/04* | (2006.01) |
| *C12Q 1/18* | (2006.01) |
| *C12Q 1/686* | (2018.01) |
| *G01N 1/31* | (2006.01) |
| *G01N 21/17* | (2006.01) |
| *G01N 21/3577* | (2014.01) |
| *G01N 21/359* | (2014.01) |
| *G01N 21/39* | (2006.01) |
| *G01N 21/45* | (2006.01) |
| *G01N 21/64* | (2006.01) |
| *G01N 21/77* | (2006.01) |
| *G01N 21/78* | (2006.01) |
| *G01N 27/414* | (2006.01) |
| *G01N 30/12* | (2006.01) |
| *G01N 30/68* | (2006.01) |
| *G01N 30/70* | (2006.01) |
| *G01N 30/72* | (2006.01) |
| *G01N 30/88* | (2006.01) |
| *G01N 33/00* | (2006.01) |
| *G01N 33/18* | (2006.01) |
| *G01N 33/50* | (2006.01) |
| *G01N 33/53* | (2006.01) |
| *G01N 33/543* | (2006.01) |
| *G01N 33/68* | (2006.01) |
| *G01N 33/74* | (2006.01) |
| *G01N 35/00* | (2006.01) |
| *G01N 35/10* | (2006.01) |
| *G06T 7/00* | (2017.01) |
| *G06T 7/90* | (2017.01) |
| *H10K 10/46* | (2023.01) |
| *H10K 85/00* | (2023.01) |
| *H10K 85/20* | (2023.01) |

(56) References Cited

U.S. PATENT DOCUMENTS

| | | | |
|---|---|---|---|
| 6,107,081 A | 8/2000 | Feeback et al. | |
| 6,204,064 B1 | 3/2001 | Alberts et al. | |
| 6,271,278 B1 | 8/2001 | Park et al. | |
| 6,287,870 B1 | 9/2001 | Wardlaw et al. | |
| 6,548,255 B2 | 4/2003 | Bensimon et al. | |
| 9,376,677 B2 | 6/2016 | Mir | |
| 10,059,990 B2 | 8/2018 | Boyden et al. | |
| 10,309,879 B2 | 6/2019 | Chen et al. | |
| 10,317,321 B2 | 6/2019 | Tillberg et al. | |
| 10,364,457 B2 | 7/2019 | Wassie et al. | |
| 10,526,649 B2 | 1/2020 | Chen et al. | |
| 10,563,257 B2 | 2/2020 | Boyden et al. | |
| 10,774,367 B2 | 9/2020 | Fraser et al. | |
| 10,995,361 B2 | 5/2021 | Chen et al. | |
| 11,180,804 B2 | 11/2021 | Chen et al. | |
| 11,408,890 B2 | 8/2022 | Boyden et al. | |
| 2002/0176880 A1 | 11/2002 | Cruise et al. | |
| 2003/0120231 A1 | 6/2003 | Wang et al. | |
| 2004/0115629 A1 | 6/2004 | Panzer et al. | |
| 2004/0137527 A1 | 7/2004 | Sleytr et al. | |
| 2004/0209317 A1 | 10/2004 | Ting | |
| 2004/0248326 A1 | 12/2004 | Ziaie et al. | |
| 2005/0034990 A1 | 2/2005 | Crooks et al. | |
| 2005/0069877 A1 | 3/2005 | Gandhi et al. | |
| 2005/0090016 A1 | 4/2005 | Rich et al. | |
| 2005/0169962 A1 | 8/2005 | Bhatia et al. | |
| 2005/0196702 A1 | 9/2005 | Bryant et al. | |
| 2006/0000767 A1 | 1/2006 | Trauger et al. | |
| 2006/0003356 A1 | 1/2006 | Shaw et al. | |
| 2006/0110760 A1 | 5/2006 | Kim et al. | |
| 2006/0115146 A1 | 6/2006 | Ogura et al. | |
| 2006/0165912 A1 | 7/2006 | Koberstein et al. | |
| 2007/0023942 A1 | 2/2007 | Andino et al. | |
| 2007/0026432 A1 | 2/2007 | Ke et al. | |
| 2007/0042954 A1 | 2/2007 | Chen et al. | |
| 2007/0134902 A1 | 6/2007 | Bertino et al. | |
| 2007/0177786 A1 | 8/2007 | Bartels | |
| 2008/0139407 A1 | 6/2008 | Slootstra et al. | |
| 2008/0261834 A1 | 10/2008 | Simon et al. | |
| 2008/0286360 A1 | 11/2008 | Shoichet et al. | |
| 2009/0011141 A1 | 1/2009 | Carter et al. | |
| 2009/0011420 A1* | 1/2009 | Barron | C08F 265/10 |
| | | | 435/6.19 |
| 2009/0096133 A1 | 4/2009 | Doyle et al. | |
| 2009/0191627 A1 | 7/2009 | Fadeev et al. | |
| 2009/0241681 A1 | 10/2009 | Machauf et al. | |
| 2010/0041128 A1 | 2/2010 | Banes et al. | |
| 2010/0055161 A1 | 3/2010 | Ahn | |
| 2010/0056445 A1 | 3/2010 | Sharma et al. | |
| 2010/0068725 A1 | 3/2010 | Armbruster et al. | |
| 2010/0096334 A1 | 4/2010 | Edmiston et al. | |
| 2010/0111396 A1 | 5/2010 | Boucheron | |
| 2010/0119755 A1 | 5/2010 | Chung et al. | |
| 2010/0248977 A1 | 9/2010 | Johnston et al. | |
| 2011/0009171 A1 | 1/2011 | Watanabe et al. | |
| 2011/0070604 A1 | 3/2011 | Gimzewski et al. | |
| 2011/0087315 A1 | 4/2011 | Richardson-Burns et al. | |
| 2011/0091717 A1 | 4/2011 | Weiss et al. | |
| 2011/0091922 A1 | 4/2011 | Krishnan et al. | |
| 2011/0291357 A1 | 12/2011 | Boyle | |
| 2012/0025271 A1 | 2/2012 | Nakano | |
| 2012/0184670 A1 | 7/2012 | Kobayashi et al. | |
| 2012/0220478 A1 | 8/2012 | Shaffer | |
| 2012/0251527 A1 | 10/2012 | Reiser | |
| 2012/0310223 A1 | 12/2012 | Knox et al. | |
| 2013/0045503 A1 | 2/2013 | Miyawaki et al. | |
| 2013/0203605 A1 | 8/2013 | Shendure et al. | |
| 2014/0087139 A1 | 3/2014 | Rowley et al. | |
| 2014/0193651 A1 | 7/2014 | Kharlampieva et al. | |
| 2014/0364330 A1 | 12/2014 | Mershin et al. | |
| 2015/0086103 A1 | 3/2015 | Tsunomori | |
| 2015/0087001 A1 | 3/2015 | Gradinaru et al. | |
| 2015/0226743 A1 | 8/2015 | Weiss et al. | |
| 2015/0353989 A1 | 12/2015 | Fraser et al. | |
| 2015/0370961 A1 | 12/2015 | Zhang et al. | |
| 2015/0376261 A1 | 12/2015 | Steyaert et al. | |
| 2016/0116384 A1* | 4/2016 | Chen | G02B 21/0072 |
| | | | 435/7.1 |
| 2016/0252528 A1 | 9/2016 | Sangaralingham et al. | |
| 2016/0265046 A1 | 9/2016 | Zhang et al. | |
| 2016/0304952 A1 | 10/2016 | Boyden et al. | |
| 2016/0305856 A1 | 10/2016 | Chen et al. | |
| 2017/0067096 A1 | 3/2017 | Wassie et al. | |
| 2017/0081489 A1 | 3/2017 | Boyden et al. | |
| 2017/0087489 A1 | 3/2017 | Sliedrecht | |
| 2017/0089811 A1* | 3/2017 | Tillberg | G01N 1/30 |
| 2017/0103521 A1 | 4/2017 | Chukka et al. | |
| 2017/0182220 A1 | 6/2017 | Song et al. | |
| 2017/0199104 A1* | 7/2017 | Gradinaru | C12Q 1/6841 |
| 2017/0276598 A1 | 9/2017 | Ikuyama | |
| 2017/0323431 A1 | 11/2017 | Sarkar et al. | |
| 2018/0119219 A1 | 5/2018 | Chen et al. | |
| 2019/0064037 A1 | 2/2019 | Boyden et al. | |
| 2019/0071656 A1 | 3/2019 | Chang et al. | |
| 2019/0113423 A1 | 4/2019 | Goodman et al. | |
| 2019/0194709 A1 | 6/2019 | Church et al. | |
| 2019/0256633 A1 | 8/2019 | Gao et al. | |
| 2020/0041614 A1 | 2/2020 | Boyden et al. | |
| 2020/0049599 A1 | 2/2020 | Alexander et al. | |
| 2020/0081005 A1 | 3/2020 | Boyden et al. | |
| 2020/0217853 A1 | 7/2020 | Estandian et al. | |

(56) References Cited

U.S. PATENT DOCUMENTS

| | | | |
|---|---|---|---|
| 2020/0271556 | A1 | 8/2020 | Sarkar et al. |
| 2020/0277664 | A1 | 9/2020 | Frenz |
| 2021/0130882 | A1 | 5/2021 | Boyden et al. |
| 2021/0190652 | A1 | 6/2021 | Quevedo et al. |

FOREIGN PATENT DOCUMENTS

| | | |
|---|---|---|
| CN | 112574089 A | 3/2021 |
| EP | 3159361 A1 | 4/2017 |
| JP | 2005291759 A | 10/2005 |
| JP | 2006036957 A | 2/2006 |
| JP | 2008286694 A | 11/2008 |
| JP | 2009191125 A | 8/2009 |
| JP | 2014005231 A | 1/2014 |
| WO | 0008212 A1 | 2/2000 |
| WO | 2007103665 A2 | 9/2007 |
| WO | 2008058302 A1 | 5/2008 |
| WO | 2010048605 A1 | 4/2010 |
| WO | 2012112689 A1 | 8/2012 |
| WO | 2012142664 A1 | 10/2012 |
| WO | 2014025392 A1 | 2/2014 |
| WO | 2014152984 A1 | 9/2014 |
| WO | 2015041755 A1 | 3/2015 |
| WO | 2015127183 A2 | 8/2015 |
| WO | 2016040489 A1 | 3/2016 |
| WO | 2017027367 A1 | 2/2017 |
| WO | 2017027368 A1 | 2/2017 |
| WO | 2017031249 | 2/2017 |
| WO | 2017079406 A1 | 5/2017 |
| WO | 2017147435 A1 | 8/2017 |
| WO | 2018157074 A1 | 8/2018 |
| WO | 2019144391 A1 | 8/2019 |
| WO | 2021051011 A1 | 3/2021 |
| WO | 2021183667 A1 | 9/2021 |
| WO | 2022100696 A1 | 3/2022 |

OTHER PUBLICATIONS

Chen, F. et al., "Supplementary Material for Expansion Microscopy", Science, 347(6221), Jan. 15, 2015, 543-548.

Goor, Olga J. et al., "Introduction of anti-fouling coutings at the surface of supramolecular elastomeric materials via post-modification of reactive supramolecular additives", Polymer Chem., vol. 8, No. 34, Jan. 1, 2017, 5228-5238.

Yu, C-C et al., "Expansion microscopy of C. elegans", ELIFE, [Online] DOI: 10.7554/eLife.46249. Retrieved from the Internet: URL:https://elifesciences.org/articles/46249> [retrieved on Feb. 26, 2021], May 1, 2020, pp. 125.

Boutin, J. A. "Myristoylation." Cell. Signal, 9(1):15-35. (Jan. 1997) doi:10.1016/S0898-6568(96)00100-3.

Bullock, G. R. "The current status of fixation for electron microscopy: A review." J. Microsc., 133: 1-15. (1984). doi:10.1111/j.1365-2818.1984.tb00458.x.

Chen, X et al. [Supplementary material] "AT AC-see reveals the accessible genome by transposase-mediated imaging and sequencing," Nature Methods, vol. 13, No. 12, Oct. 17, 2016, 1813-1828.

Cochilla, A. J. et al. "Monitoring secretory membrane with FM1-43 flourescence." Annu, Rev, Neurosci. 22:1-10 (1999). doi:10.1146/annurev.neuro.22.1.1.

Danilczyk, U. G., et al. "Functional relationship between calreticulin, calnexin, and the endoplasmic reticulum luminal domain of calnexin." J. Biol. Chem. 275(17): 13089-13097 (2000). doi:10.1074/jbc.275.17.13089.

Duan, C. et al., "Application of antigen retrieval method in hMAM immunohistochemical staining of old paraffin-embedded specimens," Academy of Military Medical Sciences, vol. 38(12), Dec. 31, 2014, 965-967.

English, A. R. et al. "Endoplasmic reticulum structure and interconnections with other organelles." Cold Spring Harbor Perspectives in Biology 2013;5:a013227. doi:10.1101/cshperspect.a013227.

Guo A. et al. "The Critical Role of Surface Chemistry in Protein Microarrays" in Functional Protein Microarrays in Drug Discovery, edt. Paul Predki, p. 53-71 (CRC press, Boca Raton, 2007).

Guo H. et al. "An efficient procedure for protein extraction from formalin-fixed, Paraffin-embedded tissues for reverse phase protein arrays." Proteome Sci. 10:56 (2012). doi:10.1186/1477-5956-10-56.

Honig, M. G. et al. "Dil and DiO: versatile fluorescent dyes for neuronal labeling and pathway tracing." Trends Neurosci. 12(9):333-341 (1989). doi:10.1016/0166-2236(89)90040-4.

Honig, M. G. et al. "Fluorescent carbocyanine dyes allow living neurons of identified origin to be studied in long-term cultures." J. Cell Biol. 103:171-187 (1986). doi:10.1083/jcb.103.1.171.

International Search Report and Written Opinion from the International Searching Authority dated Sep. 13, 2018 from corresponding International Patent Application No. PCT/US2018/41930 Filed on Jul. 13, 2018.

Jamur, M. C. et al. "Permeabilization of Cell Membranes." in Immunocytochemical Methods and Protocols 588:63-6 (2010). doi:10.1007/978-1-59745-324-0_9.

Ku, T. et al. "Multiplexed and scalable super-resolution imaging of three-dimensional protein localization in size-adjustable tissues." Nat. Biotechnol. 34(9): 973-981 (2016). doi:10.1038/nbt.3641.

Lakkaraju, A. K. K. et al. "Palmitoylated calnexin is a key component of the ribosome-translocon complex." EMBO J. 31, 1823-1835 (2012). doi:10.1038/emboj.2012.15.

Linder, M. E. et al. "Palmitoylation: Policing protein stability and traffic." Nature Reviews Molecular Cell Biology 8:74-84 (2007). doi:10.1038/nrm2084.

Mabrey, S. et al. "Investigation of phase transitions of lipids and lipid mixtures by sensitivity differential scanning calorimetry." Proc. Natl. Acad. Sci. 73(11): 3862-3866 (1976). doi:10.1073/pnas.73.11.3862.

Menon, A. K. "Lipid modifications of proteins." in 'Biochemistry of Lipids, Lipoproteins and Membranes' 39-58 (2008). doi:10.1016/8978-044453219-0.50004-0.

Myhill, N. et al. "The subcellular distribution of calnexin is mediated by PACS-2." Mol, Biol. Cell 19:2777-2788 (2008). doi:10.1091/mbc.E07-10-0995.

Revelo, N. H. et al. "A new probe for super-resolution imaging of membranes elucidates trafficking pathways." J. Cell Biol. 205(4):591-606 (2014). doi:10.1083/jcb.201402066.

Sarrazin, S. et al. "Heparan sulfate proteoglycans." Cold Spring Harb. Perspect. Biol. 2011;3:a004952. doi:10.1101/cshperspect.a004952.

Scicchitano, M. S., et al. "Protein extraction of formalin-fixed, paraffin-embedded tissue enables robust proteomic profiles by mass spectrometry." J. Histochem. Cytochem. 57(9): 849-860 (2009). doi:10.1369/jhc.2009.953497.

Seifert, U. "Configurations of fluid membranes and vesicles." Adv. Phys. 46(1):13-137 (1997). doi:10.1080/00018739700101488.

Shen, K., et al. "Comparison of different buffers for protein extraction from formalin-fixed and paraffin-embedded tissue specimens." PLoS One 10(11): e0142650 (2015). doi:10.1371/journal.pone.0142650.

Shi, S. R., et al. "Antigen retrieval in formalin-fixed, paraffin-embedded tissues: An enhancement method for immunohistochemical staining based on microwave oven heating of tissue sections." J. Histochem. Cytochem. 39 (6):741-8 (1991) doi:10.1177/39.6.1709656.

Tanca, A. et al. "Comparability of differential proteomics data generated from paired archival fresh-frozen and formalin-fixed samples by GeLC-MS/MS and spectral counting." J. Proteomics 77:561-576 (2012). doi:10.1016/j.jprof.2012.09.033.

Tanca, A. et al. "Critical comparison of sample preparation strategies for shotgun proteomic analysis of formalin-fixed, paraffin-embedded samples: Insights from liver tissue." Clin. Proteomics 11:28 (2014). doi:10.1186/1559-0275-11-28.

Testagrossa et al. "Immunohistochemical expression of podocyte markers in the variants of focal segmental glomerulosclerosis." National Dial Transplant 28: 91-98 (2013).

ThermoFisher Scientific, Epitope Recovery Methods for IHC, Nov. 7, 2015, pp. 1-2,.

(56) References Cited

OTHER PUBLICATIONS

Valenzuela, J. I. et al. "Diversifying the secretory routes in neurons." Frontiers in Neuroscience 9:358 (2015). doi:10.3389/fnins.2015.00358.
Van Meer, G., et al. "Membrane lipids: Where they are and how they behave." Nature Reviews Molecular Cell Biology 9(2): 112-124 (2008). doi:10.1038/nrm2330.
Wassie, A. T., et al. "Expansion microscopy: principles and uses in biological research." Nature Methods 16(1): 33-41 (2019). doi:10.1038/s41592-018-0219-4.
Weber, P. C., et al. "Structural origins of high-affinity biotin binding to streptavidin." Science 243(4887):85-88 (1989). doi:10.1126/science.2911722.
Wen, G. et al. "Evaluation of direct grafting strategies in Expansion Microscopy." BioRxiv preprint Jul. 8, 2019. doi: https://doi.org/10.1101/696039 (Jul. 8, 2019).
Wurm, C. A. et al. "Nanoscale distribution of mitochondrial import receptor Tom20 is adjusted to cellular conditions and exhibits an inner-cellular gradient." Proc. Natl. Acad. Sci. U. S. A. 108(33):13546-13551 (2011). doi:10.1073/pnas.1107553108.
Yan, B. X. et al. "Glycine residues provide flexibility for enzyme active sites." J. Biol. Chem. 272(6): 3190-4 (1997). doi:10.1074/jbc.272.6.3190.
Zhao, Y. et al. "Nanoscale imaging of clinical specimens using pathology-optimized expansion microscopy." Nat. Biotechnol. 35(8): 757-764 (2017). doi:10.1038/nbt.3892.
Zuiderveld, K. "Contrast Limited Adaptive Histogram Equalization." in Graphics Gems 474-485 (1994). doi:10.1016/b978-0-12-336156-1.50061-6.
New England BioLabs, "Proteinase K", P8102S product datasheet, 1 page, accessed Nov. 17, 2020.
Office Action dated Apr. 4, 2018 from U.S. Appl. No. 14/627,310, filed Feb. 20, 2015.
Product information brochure, Flocryltm MBA, SNF Floerger, pp. 1-4, accessed Nov. 17, 2020.
"Crosslinking and Photoactivatable Reagents", Invitrogen, Chapter 5 in "Molecular Probes™ Handbook A Guide to Fluorescent Probes and Labeling Technologies", 11th Edition, 2010, 171-188.
"Epitope Recovery Methods for IHC", Nov. 7, 2015, ThermoFisher Scientific, pp. 1-2.
"Proteinase K from Tritirachium album, solution", Serva Electrophoresis, Instruction Manual, Cat. No. 33755, 1 page, publicly available prior to Feb. 1, 2017.
Al, H. et al., "Exploration of new chromophore structures leads to the identification of improved blue fluorescent proteins", Biochemistry, 46, 2007, 5904-10.
Akhavan, A. et al., "Molecular Epizootiology of Rodent Leishmaniasis in a Hyperendemic Area of Iran", Iranian J Publ Health, vol. 39, No. 1, 2010, 1-7.
Bates, M. et al., "Multicolor super-resolution imaging with photoswitchable fluorescent probes", Science, 317, 2007, 1749-1753.
Batish, M. et al., "Neuronal mRNAs Travel Singly into Dendrites", PNAS, vol. 109(12), 2012, 4645-4650.
Beliveau, B. et al., "Versatile design and synthesis platform for visualizing genomes with Oligopaint FISH probes", PNAS, vol. 109(52): pfa, 2012, 21301-21306.
Bi, X. et al., "In situ-forming cross-linking hydrogel systems: chemistry and biomedical applications", In: "Emerging Concepts in Analysis and Applications of Hydrogels", INTECH, Aug. 24, 2016, 131-158.
Bleckmann, J. et al., "Surface-Layer Lattices as Patterning Element for Multimeric Extremozymes", Small Journal, 2013, 1-8.
Bokman, S. H. et al., "Renaturation of Aequorea gree-fluorescent protein", Biochem. Biophys. Res. Commun., 101, 1981, 1372-80.
Bossi, M. et al., "Multicolor far-field fluorescence nanoscopy through isolated detection of distinct molecular species", Nano Lett., 8, 2008, 2463-8.

Breitwieser, A. et al., "Magnetic Beads Functionalized with Recombinant S-Layer Protein Exhibit High Human IgG-Binding and Anti-Fouling Properties", Current Topics in Peptide & Protein Research, vol. 17, 2016, 45-55.
Bruchez, M. et al., "Semiconductor nanocrystals as fluorescent biological labels", Science, vol. 281, 1998, 2013-6.
Buckley, P. et al., "Cytoplasmic Intron Sequence-Retaining Transcripts Can Be Dendritically Targeted via ID Element Retrotransposons", Neuron, vol. 69, 2011, 877-884.
Buenrostro, J. D. et al., "ATAC-seq: A Method for Assaying Chromatin Accessibility Genome-Wide : ATAC-seq for Assaying Chromatin Accessibility", In: "Current Protocols in Molecular Biology", Wiley, New York, NY, Jan. 5, 2015.
Buxbaum, A. et al., "Single-Actin mRNA Detection in Neurons Reveals a Mechanism for Regulating its Translatability", Science, vol. 343, 2014, 419-422.
Cabili, M. et al., "Localization and abundance analysis of human lncRNAs at single-cell and single-molecule resolution", Genome Biology, vol. 16(20), 2015.
Cai, et al., Nat Meth., 10, 2013, 540-547.
Cajigas, I. et al., "The local transcriptome in the synaptic neuropil revealed by deep sequencing and high-resolution imaging", Neuron 74, 2012, 453-466.
Cao, W. , "DNA ligases and ligase-based technologies", Clinical and Applied Immunology Reviews, Elsevier, Amsterdam, NL, vol. 2, No. 1, Jan. 15, 2001, 33-43.
Carpenter, A. E. et al., "CellProfiler: image analysis software for identifying and quantifying cell phenotypes", Genome Biol., 7, 2006, R100.
Chang, J-B et al., "Iterative expansion microscopy", Nature Methods, 14(6), Jun. 2017, 593-599.
Chen, F. et al., "Expansion Microscopy", Science, 347(6621):, Jan. 15, 2015, 1-18.
Chen, F. et al., "Nanoscale Imaging of RNA with Expansion Microscopy", Nature Methods, 13(8):, Aug. 2016, 679-684.
Chen, K. et al., "Spatially resolved, highly multiplexed RNA profiling in single cells", Science. vol. 348(6233), 2015, aaa6090-aaa6090.
Choi, H. et al., "Next-Generation in Situ Hybridization Chain Reaction: Higher Gain, Lower Cost, Greater Durability", ACS Nano 8(5), 2014, 4284-4294.
Choi, H. et al., "Programmable in situ amplification for multiplexed imaging of mRNA expression", Nature Biotechnology, 28(11), 2010, 1208-1212.
Chozinski, T. et al., "Expansion microscopy with conventional antibodies and fluorescent proteins", Nature Methods, vol. 13(6), 2016, 485-491.
Chu, J. et al., "Non-invasive intravital imaging of cellular differentiation with a bright red-excitable fluorescent protein", Nat. Methods, 11, 2014, 572-8.
Clemson, C. et al., "An architectural role for a nuclear noncoding Rna: NEAT1 RNA is essential for the structure of paraspeckles", Molecular Cell, 33, 2009, 717-26.
Cormack, B. P. et al., "FACS-optimized mutants of the green fluorescent protein (GFP)", Gene, 173, 1996, 33-8.
Cubitt, A. B. et al., "Understanding structure-function relationships in the Aequorea victoria green fluorescent protein", Methods Cell Biol., 58, 1999, 19-30.
Dedecker, P. et al., "Localizer: fast, accurate, open-source, and modular software package for superresolution microscopy", J. Biomed. Opt., 17, 2012, 126008.
DiLorenzo, F. et al., "Nanostructural Heterogeneity in Polymer Networks and Gels", Polymer Chemistry, vol. 6, 2015, 5515-5528.
Edelstein, A. et al., "Computer control of microscopes using uManager", Curr. Protoc. Mol. Biol. Chapter 14, Unit14.20, 2010,.
English, B. P. et al., "A three-camera imaging microscope for high-speed single- molecule tracking and super-resolution imaging in living cells", in SPIE Nanosci. + Eng. (Mohseni, H., Agahi, M. H. & Razeghi, M.) 955008 (International Society for Optics and Photonics, 2015). doi:10.1117/12.2190246.
Engreitz, J. et al., "The Xist lncRNA exploits three-dimensional genome architecture to spread across the X chromosome", Science 341, 2013, 1237973.

(56) References Cited

OTHER PUBLICATIONS

Femino, A. et al., "Visualization of Single RNA Transcripts in Situ", Science, vol. 280, 1998, 585-590.

Feng, G. et al., "Imaging neuronal subsets in transgenic mice expressing multiple spectral variants of GFP", Neuron, 28, 2000, 41-51.

Filonov, G. S. et al., "Bright and stable near-infrared fluorescent protein for in vivo imaging", Nat. Biotechnol., 29, 2011, 757-61.

Fouz, M. et al., "Bright Fluorescent Nanotags from Bottlebrush Polymers with DNA-Tipped Bristles", ACS Central Science, vol. 1, 2015, 431-438.

Freifeld, L. et al., "Expansion microscopy of zebrafish for neuroscience and developmental biology studies", PNAS (online), Nov. 21, 2017, E10799-E10808.

Goedhardt, J. et al., "Structure-guided evolution of cyan fluorescent proteins towards a quantum yield of 93%", Nat. Commun., 3, Jan. 1, 2017, 751.

Griesbeck, O. et al., "Reducing the environmental sensitivity of yellow fluorescent protein. Mechanism and applications", J. Biol. Chem., 276, 2001, 29188-94.

Gurskaya, N. G. et al., "Engineering of a monomeric green-to-red photoactivatable fluorescent protein induced by blue light", Nat. Biotechnol., 24, 2006, 461-5.

Gyorvary, E. S. et al., "Self-Assembly and Recrystallization of Bacterial S-Layer Proteins at Silicon Supports Imaged in Real Time by Atomic Force Microscopy", Journal of Microscopy, vol. 212, 2003, 300-306.

Habuchi, S. et al., "mKikGR, a monomeric photoswitchable fluorescent protein", PLoS One, 3, 2008, e3944.

Hackstadt, T., "Steric hindrance of antibody binding to surface proteins of *Coxiella burnetti* by phase I lipopolysaccharide", Infect Immun, 56, 1998, 802-807.

Heim, R. et al., "Engineering green fluorescent protein for improved brightness, longer wavelengths and fluorescence resonance energy transfer", Curr. Biol., 6, 1996, 178-82.

Heim, R. et al., "Wavelength mutations and posttranslational autoxidation of green fluorescent protein", Proc. Natl. Acad. Sci. U.S.A., 91, 1994, 12501-4.

Hoffman, T. L. et al., "A Biosensor Assay for Studying Ligand-Membrane Receptor Interactions: Binding of Antibodies and HIV-1 Env to Chemokine Receptors", PNAS, 97(21), 2000, 11215-11220.

Huang, B. et al., "Whole-cell 3D Storm reveals interactions between cellular structures with nanometer-scale resolution", Nat. Methods, 5, 2008, 1047-1052.

Huisken, J. et al., "Optical Sectioning Deep Inside Live Embryos by Selective Plane Illumination Microscopy", Science. vol. 305, 2004, 1007-1009.

Hunt, et al., "High temperature antigen retrieval and loss of nuclear morphology: a comparison of microwave\rand autoclave techniques", J. Clin. Pathol. 49, 1996, 767-770.

Jekel, P A. et al., "Use of endoproteinase Lys-C from Lysobacter enzymogenes in protein sequence analysis", Anal. Biochem., 134, 1983, 347-354.

Jiang, Y. et al., "Click hydrogels, microgels and nanogels: emerging platforms for drug delivery and tissue engineering", Biomaterials, vol. 35, No. 18, Jun. 1, 2014, 4969-4985.

Jimenez, N. et al., "A Novel Approach for Intracellular 3D Immuno-Labeling for Electron Tomography", Traffic, 13, 2012, 926-933.

Jung, H. et al., "Axonal mRNA localization and local protein synthesis in nervous system assembly, maintenance and repair", Nat. Rev. Neurosci., vol. 13(5), 2012, 308-24.

Kakimoto, K. et al., "Hypothesis for the mechanism for heat-induced antigen retrieval occurring on fresh frozen sections without formalin-fixation in immunohistochemistry", J Mol Histol., 39, 2008, 389-399.

Kaur, et al., Biochemistry 45, 2006, 7347-7355.

Ke, R. et al., "In situ sequencing for RNA analysis in preserved tissue and cells", Nature Methods, vol. 10(9), 2013, 857-60.

Ke, Rongqin et al., "Supplementary Material in situ sequencing for RNA analysis in preserved tissue and cells", Nature Methods 10(9):857-60, 2013, 1-29.

Kroon, D.-J , "B-spline Grid, Image and Point based Registration", Matlab Cent. at <http://www.mathworks.com/matlabcentral/fileexchange/20057-b-spline-grid-image-and-point-based-registration>.

Laemmli, U. K., "Cleavage of structural proteins during the assembly of the head of bacteriophage T4", Nature, 227, 1970, 680-685.

Lam, A. J. et al., "Improving FRET dynamic range with bright green and red fluorescent proteins", Nat. Methods, 9, 2012, 1005-12.

Lee, J. H. et al., "Highly Multiplexed Subcellular RNA Sequencing in Situ", Sciencexpress, online http://www.sciencemag.org/content/early/recent, 6 pages (Science, vol. 343), Feb. 27, 2014.

Lein, E. et al., "Genome-wide atlas of gene expression in the adult mouse brain", Nature, vol. 445, 2007, 168-76.

Levsky, J. et al., "Fluorescence in situ hybridization: past, present and future", Journal of Cell Science, 116, 2003, 2833-2838.

Lieberman-Aiden, E. et al., "Comprehensive mapping of long-range interactions reveals folding principles of the human genome", Science 326, 2009, 289-93.

Livet, J. et al., "Transgenic strategies for combinatorial expression of fluorescent proteins in the nervous system", Nature, 450, 2007, 56-62.

Lowe, D. G., "Distinctive Image Features from Scale-Invariant Keypoints", Int. J. Comput. Vis., 60, 2004, 91-110.

Lubeck, E. et al., "Single-cell in situ RNA profiling by sequential hybridization", Nature Methods, vol. 11(4), 2014, 360-1.

Lubeck, E. et al., "Single-cell systems biology by super-resolution imaging and combinatorial labeling", Nature Methods, vol. 9, 2012, 743-8.

Majcher, M. J. et al., "Hydrogel synthesis and design", In: "Cellulose-Based Superabsorbent Hydrogels", Springer International Publishing, Jan. 1, 2018, 1-41.

Markwardt, M. L. et al., "An improved cerulean fluorescent protein with enhanced brightness and reduced reversible photoswitching", PLoS One, 6, 2011, e17896.

McKinney, S. A. et al., "A bright and photostable photoconvertible fluorescent protein", Nat. Methods, 6, 2009, 131-3.

Meng, H., "Localization of a Blood Pressure Quantitative Trait Locus (QTL) to a 1.7cM Interval on Rat Chromosome 9", Medical College of Ohio, dissertation, 2002, 1-158.

Mito, M. et al., "Simultaneous multicolor detection of RNA and proteins using super-resolution microscopy", Methods, doi:10.1016/j.ymeth.2015.11.007., 2015.

Mortensen, K. I. et al., "Optimized localization analysis for singlemolecule tracking and super-resolution microscopy", Nat. Methods, 7, 2010, 377-81.

Nagai, T. et al., "A variant of yellow fluorescent protein with fast and efficient maturation for cell-biological applications", Nat. Biotechnol., 20, 2002, 87-90.

Nagre, R. D. et al., "Thermosaline Resistant Acrylamide-Based Polyelectrolyte as Filtration Control Additive in Aqueous-Based Mud", Petroleum and Coal, vol. 56, No. 3, 2014, 222-230.

Nilsson, M. et al., "RNA-templated DNA ligation for transcript analysis", Nucleic Acids Research, Information Retrieval LTD., vol. 29, No. 2, Jan. 15, 2001, 578-581.

Orakdogen, N. et al., "Correlation Between Crosslinking Efficiency and Spatial Inhomogeneity in Poly(acrylamide) Hydrogels", Polymer Bulletin, vol. 57, 2006, 631-641.

Ormo, M. et al., "Crystal structure of the Aequorea victoria green fluorescent protein", Science, 273, 1996, 1392-5.

Oshima, K. et al., "Model Polyelectrolyte Gels Synthesized by End-Linking of Tetra-Arm Polymers with Click Chemistry: Synthesis and Mechanical Properties", Macromolecules, vol. 47, 2014, 7573-7580.

Panning, B. et al., "X chromosome Inactivation is Mediated by by Xist RNA stabilization", Cell. vol. 90, 1997, 907-16.

Parang, B. et al., "Myeloid translocation genes differentially regulate colorectal cancer programs", Oncogene, vol. 35, 2016, 6341-6349.

(56) References Cited

OTHER PUBLICATIONS

Park, Y. N. et al., "Detection of Hepatitis C Virus RNA Using Ligation-Dependent Polymerase Chain Reaction in Formalin-Fixed, Paraffin-Embedded Liver Tissues", Amer. J. of Pathol., vol. 149, No. 5, Nov. 1, 1996, 1485-1491.
Plath, K. et al., "Xist RNA and the mechanism of X chromosome inactivation", Annu. Rev. Genet. 36, 2002, 233-78.
Pum, D. et al., "Reassembly of S-Layer Proteins", Nanotechnology, 2014, 1-15.
Raj, A. et al., "Detection of individual endogenous RNA transcripts in situ using multiple singly labeled probes", Methods in Enzymology, vol. 472 (Elsevier Inc.), 2010, 365-386.
Raj, A. et al., "Imaging individual mRNA molecules using multiple singly labeled probes", Nat. Methods 5(10), 2008, 877-879.
Randall, K. J. et al., "A dual-label technique for the immunohistochemical demonstration of T-lymphocyte subsets in formalin-fixed, paraffin-embedded rat lymphoid tissue", Toxicol. Pathol., 36, 2008, 795-804.
Rego, E. H. et al., "Nonlinear structured-illumination microscopy with a photoswitchable protein reveals cellular structures at 50-nm resolution", Proc. Natl. Acad. Sci. U.S.A., 109, 2012, E135-43.
Reinhart-King, C. A. et al., "Dynamics and Mechanics of EndothelialCell Spreading", Biophysical J, 89(1):, Jul. 1, 2005, 676-689.
Rose, R. et al., "Ocular ascorbate transport and metabolism", A. Comp. Physiol., 100, 1991, 273-85.
Rothbauer, M. et al., "Exploitation of S-Layer Anisotropy: pH-Dependent Nanolayer Orientation for Cellular Micropatterning,", Acs NANO, published online, 2013.
Sakai, T. et al., "Design and Fabrication of a High-Strength Hydrogel with Ideally Homogenous Network Structure from Tetrahedron-Like Macromonomers", Macromolecules, vol. 41, 2008, 5379-5384.
Schindelin, J. et al., "Fiji: an open-source platform for biological-image analysis", Nature Methods, vol. 9, 2012, 676-82.
Schnell, U. et al., "Immunolabeling artifacts and the need for live-cell imaging", Nat. Methods, 9, 2012, 152-158.
Seneviratne, U. et al., "S-nitrosation of proteins relevant to Alzheimer's disease during early stages of neurodegeneration", Proc. Natl. Acad. Sci. U. S. A. 1521318113—(2016). doi:10.1073/pnas.1521318113.
Shah, S. et al., "Single-molecule RNA detection at depth via hybridization chain reaction and tissue hydrogel embedding and clearing", Development in Review, 2016.
Shaner, N. C. et al., "Improved monomeric red, orange and yellow fluorescent proteins derived from *Discosoma* sp. red fluorescent protein", Nat. Biotechnol., 22, 2004, 1567-72.
Shaner, N. C. et al., "Improving the photostability of bright monomeric orange and red fluorescent proteins", Nat. Methods, 5, 2008, 545-51.
Shcherbakova, D. M. , "An orange fluorescent protein with a large Stokes shift for single-excitation multicolor FCCS and FRET imaging", J. Am. Chem. Soc., 134, 2012, 7913-23.
Shcherbo, D. et al., "Far-red fluorescent tags for protein imaging in living tissues", Biochem. J., 418, 2009, 567-74.
Sleytr, U. et al., "Heterologous Reattachment of Regular Arrays of Glycoproteins on Bacterial Surfaces", Nature, vol. 257, 1975, 400-401.
Sleytr, U. et al., "S-Layers Principles and Applications", FEMS Microbiology Rev., 2014, 1-42.
Sniegowski, J. A. et al., "Maturation efficiency, trypsin sensitivity, and optical properties of Arg96, Glu222, and Gly67 variants of green fluorescent protein", Biochem. Biophys. Res. Commun., 332, 2005, 657-63.
Steward, O. et al., "Compartmentalized synthesis and degradation of proteins in neurons", Neuron, vol. 40, 2003, 347-359.
Steward, O. et al., "Synaptic activation causes the mRNA for the leg Arc to localize selectively near activated postsynaptic sites on dendrites", Neuron, vol. 21, 1998, 741-751.
Strack, R. , "Imaging Bigger is Better for Super-Resolution", Nature Methods, 12(13), Mar. 1, 2015, 169.
Subach, F. V. et al., "Bright monomeric photoactivatable red fluorescent protein for two-color super-resolution sptPALM of live cells", J. Am. Chem. Soc., 132, 2010, 6481-91.
Subach, O. M. et al., "An Enhanced Monomeric Blue Fluorescent Protein with the High Chemical Stability of the Chromophore", PLoS One, 6, 2011, e28674.
Thevenaz, P. et al., "A pyramid approach to subpixel registration based on intensity", IEEE Trans. Image Process., 7, 1998, 27-41.
Tillberg, P. et al., "Protein-Retention Expansion Microscopy of Cells and Tissues Labeled Using Standard Fluorescent Proteins and Antibodies", Nature Biotechnology vol. 34(9), 2016, 987-995.
Van Vliet, et al., "The Biomechanics Toolbox: Experimental Approaches for Living Cells and Biomolecules", Acta Materialia, 51, Aug. 23, 2003, 5881-5905.
Vedaldi, A. et al., Vlfeat. in Proc. Int. Conf. Multimed. —MM '10 1469 (ACM Press, 2010). doi:10.1145/1873951.1874249.
Wachter, R. M. et al., "Sensitivity of the yellow variant of green fluorescent protein to halides and nitrate", Curr. Biol., 9, 1999, R628-R629.
Wang, F. et al., "RNAscope: A novel in situ RNA analysis platform for formalin-fixed, paraffin-embedded tissues", Journal of Molecular Diagnostics, vol. 14(1), 2012, 22-29.
Wu, C. C. et al., "A method for the comprehensive proteomic analysis of membrane proteins", Nat. Biotechnol., 21, 2003, 532-8.
Xingqi, C. et al., "ATAC-see reveals the accessible genome by transposase-mediated HJ, imaging and sequencing", Nature Methods, vol. 13, No. 12, Dec. 1, 2016, 1013-1020.
Xu, J. et al., "Bioorthogonally cross-linked hydrogel network with precisely controlled disintegration time over a broad ragne", J. Am. Chem.Soc., vol. 136, No. 11, Mar. 19, 2014, 4105-4108.
Yazici, I. et al., "Spatial Inhomogeneity in Poly(acrylic acid) Hydrogels", Polymer, vol. 46, 2005, 2595-2602.
Zhang, D. et al., "Dynamic DNA nanotechnology using strand-displacement reactions", Nature Chemistry, vol. 3, 2011, 103-113.
Zhang, R. et al., "Tools for GPCR Drug Discovery", Acta Pharmacologica Sinica, 33, 2012, 372-384.
Zhou, C. et al., "Synthesis and characterization of well-defined PAA-PEG multi-responsive hydrogels by ATRP and click chemistry", RSC Adv., vol. 4, No. 97, Jan. 1, 2014, 54631-54640.
Zimmerman, T. A. et al., "Adapting the stretched sample method from tissue profiling to imaging", Proteomics, 8, 2008, 3809-3815.
Alon, S. et al. Expansion sequencing: Spatially precise in situ transcriptomics in intact biological systems. Science 371, 481-+, doi:10.1126/science.aax2656 (2021).
Cahoon, C. K. et al. Superresolution expansion microscopy reveals the three-dimensional organization of the *Drosophila synaptonemal* complex. Proc Natl Acad Sci U S A 114, E6857-E6866, doi:10.1073/pnas.1705623114 (2017).
Campbell, K. R. et al. clonealign: statistical integration of independent single-cell RNA and DNA sequencing data from human cancers. Genome Biol 20, 54, doi:10.1186/s13059-019-1645-z (2019).
Chen, G. et al. Reactivity of functional groups on the protein surface: development of epoxide probes for protein labeling. J Am Chem Soc 125, 8130-8133, doi:10.1021/ja034287m (2003).
Cirillo, L. et al. UBAP2L forms distinct cores that act in nucleating stress granules upstream of G3BP1. Curr Biol 30, 698-707 e696, doi:10.1016/j.cub.2019.12.020 (2020).
Cote, A. et al. The spatial distributions of pre-mRNAs suggest post-transcriptional splicing of specific introns within endogenous genes. bioRxiv, doi:10.1101/2020.04.06.028092 (2020).
Cui, Y. et al. Fluctuation localization imaging-based fluorescence in situ hybridization (fliFISH) for accurate detection and counting of RNA copies in single cells. Nucleic Acids Res 46, e7, doi:10.1093/nar/gkx874 (2018).
Cui, Y. et al. Quantitative mapping of oxidative stress response to lithium cobalt oxide nanoparticles in single cells using multiplexed in situ gene expression analysis. Nano Lett 19, 1990-1997, doi:10.1021/acs.nanolett.8b05172 (2019).
Decarreau, J. et al. Corrigendum: The tetrameric kinesin Kif25 suppresses pre-mitotic centrosome separation to establish proper spindle orientation. Nat Cell Biol 19, 740, doi:10.1038/ncb3546 (2017).

(56) References Cited

OTHER PUBLICATIONS

Decarreau, J. et al. The tetrameric kinesin Kif25 suppresses premitotic centrosome separation to establish proper spindle orientation. Nat Cell Biol 19, 384-390, doi:10.1038/ncb3486 (2017).
Eirew, P. et al. Dynamics of genomic clones in breast cancer patient xenografts at single-cell resolution. Nature 518, 422-426, doi:10.1038/nature13952 (2015).
Falahati, H. et al., Thermodynamically driven assemblies and liquid-liquid phase separations in biology. Soft Matter 15, 1135-1154, doi:10.1039/c8sm02285b (2019).
Fecher, C. et al. Cell-type-specific profiling of brain mitochondria reveals functional and molecular diversity. Nat Neurosci 22(10), 1731-1742 doi:10.1038/s41593-019-0479-z (2019).
Gambarotto, D. et al. Imaging cellular ultrastructures using expansion microscopy (U-ExM). Nat Methods 16, 71-74, doi:10.1038/s41592-018-0238-1 (2019).
Gao, M. et al. Expansion stimulated emission depletion microscopy (ExSTED). ACS Nano 12, 4178-4185, doi:10.1021/acsnano.8b00776 (2018).
Gao, R. et al. A highly homogeneous polymer composed of tetrahedron-like monomers for high-isotropy expansion microscopy. Nat Nanotechnol 16, 698-707, doi:10.1038/s41565-021-00875-7 (2021).
Gao, R. et al. Cortical column and whole-brain imaging with molecular contrast and nanoscale resolution. Science 363 (6424), doi:10.1126/science.aau8302 (2019).
Hafner, A. S. et al., Local protein synthesis is a ubiquitous feature of neuronal pre- and postsynaptic compartments. Science 364, doi:10.1126/science.aau3644 (2019).
Halpern, A. R. et al., Hybrid structured illumination expansion microscopy reveals microbial cytoskeleton organization. ACS Nano 11, 12677-12686, doi:10.1021/acsnano.7b07200 (2017).
Hansen, M., Lee, S. J., Cassady, J. M. & Hurley, L. H. Molecular details of the structure of a psorospermin-DNA covalent/intercalation complex and associated DNA sequence selectivity. J Am Chem Soc 118, 5553-5561 (1996).
He, J. et al. Prevalent presence of periodic actin-spectrin-based membrane skeleton in a broad range of neuronal cell types and animal species. Proc Natl Acad Sci U S A 113, 6029-6034, doi:10.1073/pnas.1605707113 (2016).
Invitrogen Corporation, "Proteinase K (solution), RNA Grade", Cat. No. 25530-049, rev. date: Aug. 25, 2008, 2 pages, accessed from https://www.thermofisher.com/document-connect/document-connect.html?url=https://assets.thermofisher.com/TFS-Assets%2FLSG%2Fmanuals%2Fproteinasek_solution_man.pdf (2008).
Kao, P. et al., Transcriptional activation of *Arabidopsis zygotes* is required for initial cell divisions. Sci Rep 9, 17159, doi:10.1038/s41598-019-53704-2 (2019).
Karagiannis, E. D. et al. Expansion microscopy of lipid membranes. bioRxiv, 829903, doi:10.1101/829903 (2019).
Keenan et al., "An automated machine vision system for the histological grading of cervical intraepithelial neoplasia (CIN)," Journal of Pathology, J Pathol 2000; 192: pp. 351-362.
Koppers, M. et al. Receptor-specific interactome as a hub for rapid cue-induced selective translation in axons. Elife 8, 1-27 doi:10.7554/eLife.48718 (2019).
Kumar, A. et al. Influenza virus exploits tunneling nanotubes for cell-to-cell spread. Sci Rep 7, 1-14, 40360, doi:10.1038/srep40360 (2017).
Kunz, T. C. et al., Using Expansion Microscopy to Visualize and Characterize the Morphology of Mitochondrial Cristae. Front Cell Dev Biol 8, 617, doi:10.3389/fcell.2020.00617 (2020).
Li, R. et al., Expansion enhanced nanoscopy. Nanoscale 10, 17552-17556, doi:10.1039/c8nr04267e (2018).
Lim, Y. et al. Mechanically resolved imaging of bacteria using expansion microscopy. PLoS Biol 17, e3000268, doi:10.1371/journal.pbio.3000268 (2019).
Martinez, G. F. et al. Quantitative expansion microscopy for the characterization of the spectrin periodic skeleton of axons using fluorescence microscopy. Sci Rep 10, 2917, doi:10.1038/s41598-020-59856-w (2020).
Mosca, T. J. et al., Presynaptic LRP4 promotes synapse number and function of excitatory CNS neurons. Elife 6, doi:10.7554/eLife.27347 (2017).
M'Saad, O. et al., Light microscopy of proteins in their ultrastructural context. Nat Commun 11, 3850, doi:10.1038/s41467-020-17523-8 (2020).
Park, Y. G. et al. Protection of tissue physicochemical properties using polyfunctional crosslinkers. Nat Biotechnol 37, 73-83 , doi:10.1038/nbt.4281 (2019).
Richter, S. et al. Clerocidin alkylates DNA through its epoxide function: evidence for a fine tuned mechanism of action. Nucleic Acids Res 31, 5149-5156, doi:10.1093/nar/gkg696 (2003).
Sahl, S. J. et al., Fluorescence nanoscopy in cell biology. Nat Rev Mol Cell Biol 18(11), 685-701, doi:10.1038/nrm.2017.71 (2017).
Sarkar, D. et al. Expansion revealing: decrowding proteins to unmask invisible brain nanostructures. bioRxiv, doi:10.1101/2020.08.29.273540 (2020).
Shen, F. Y. et al. Light microscopy based approach for mapping connectivity with molecular specificity. Nat Commun 11, 4632, doi:10.1038/s41467-020-18422-8 (2020).
Shurer, C. R. et al. Physical principles of membrane shape regulation by the glycocalyx. Cell 177, 1757-1770 e1721, doi:10.1016/j.cell.2019.04.017 (2019).
Sidenstein, S. C. et al. Multicolour multilevel STED nanoscopy of actin/spectrin organization at synapses. Sci Rep 6, 26725, doi:10.1038/srep26725 (2016).
So, C. et al. A liquid-like spindle domain promotes acentrosomal spindle assembly in mammalian oocytes. Science 364, doi:10.1126/science.aat9557 (2019).
Suofu, Y. et al. Dual role of mitochondria in producing melatonin and driving GPCR signaling to block cytochrome c release. Proc Natl Acad Sci U S A 114, E7997-E8006, doi:10.1073/pnas.1705768114 (2017).
Thevathasan, J. V. et al. Nuclear pores as versatile reference standards for quantitative superresolution microscopy. Nat Methods 16, 1045-1053, doi:10.1038/s41592-019-0574-9 (2019).
Tillberg, P. W. et al. Expansion microscopy: scalable and convenient super-resolution microscopy. Annu Rev Cell Dev Biol 35, 683-701, doi:10.1146/annurev-cellbio-100818-125320 (2019).
Truckenbrodt et al., A practical guide to optimization in X10 expansion microscopy. Nat Protoc 14, 832-863, doi:10.1038/s41596-018-0117-3 (2019).
Valdes, P. A. et al. Decrowding expansion pathology: unmasking previously invisible nanostructures and cells in intact human brain pathology specimens. bioRxiv, doi: 10.1101/2021.12.05.471271 (2021).
Wang, G. et al., Multiplexed imaging of high-density libraries of RNAs with MERFISH and expansion microscopy. Sci Rep 8(4847), 1-13 doi:10.1038/s41598-018-22297-7 (2018).
Wang, Y. et al. EASI-FISH for thick tissue defines lateral hypothalamus spatio-molecular organization. Cell 184, 6361-6377 e6324, doi:10.1016/j.cell.2021.11.024 (2021).
Xu, H. et al. Molecular organization of mammalian meiotic chromosome axis revealed by expansion STORM microscopy. Proc Natl Acad Sci U S A 116, 18423-18428, doi:10.1073/pnas.1902440116 (2019).
Xu, K. et al., Actin, spectrin, and associated proteins form a periodic cytoskeletal structure in axons. Science 339, 452-456, doi:10.1126/science.1232251 (2013).
Caprette, "Experimental Biosciences: Resources for Introductory & Intermediate level laboratory courses" (2012), available online at https://www.ruf.rice.edu/~bioslabs/studies/sds-page/denature.html (Year: 2012).
Cho et al., "Expansion Microscopy" (2018), Journal of Microscopy, vol. 271, Issue 2: 123-128. (Year: 2018).
Ferri, A., "Expansion Microscopy: A New Approach to Microscopic Evaluation", Master's thesis, retrieved from https://scholarcommons.sc.edu/etd/6034, 2020.
Neely, R.K. et al., "Optical mapping of DNA: Single-molecule-based methods for mapping genomes." Biopolymers 95.5 (2011): 298-311.
Akhmetzhan, A., et al. "A short review on the N, N-Dimethylacrylamide-based hydrogels." Gels 7.4 (2021): 234.

(56) References Cited

OTHER PUBLICATIONS

Cipriano, B.H., et al. "Superabsorbent hydrogels that are robust and highly stretchable." Macromolecules 47.13 (2014): 4445-4452.
Klimas, A., et al. "Magnify is a universal molecular anchoring strategy for expansion microscopy." Nature biotechnology 41.6 (2023): 858-869.
Rueda, J.C., et al. "Synthesis and characterization of stiff, self-crosslinked thermoresponsive DMAA hydrogels." Polymers 12.6 (2020): 1401.
Truckenbrodt, S., et al. "X10 expansion microscopy enables 25-nm resolution on conventional microscopes." EMBO reports 19.9 (2018): e45836.
Abbasi et al., Palmitic Acid-Modified Poly-L-Lysine for Non-Viral Delivery of Plasmid DNA to Skin Fibroblasts, 2007, Biomacromolecules 2007, 8, 1059-1063 (Year: 2007).
Abcam, "IHC-Paraffin Protocol (IHC-P)", 13 pages, published: Jun. 15, 1999, online webpage: www.abcam.com/ps/pdf/protocols/ihc_p.pdf. (Year: 1999).
Ahearn et al., Posttranslational Modifications of RAS Proteins, Cold Spring Harb Perspect Med 2018;8:a031484 (Year: 2018).
Bensimon, A. et al., "Alignment and Sensitive Detection of DNA by a Moving Interface." Alignment and Sensitive Detection of DNA by a Moving Interface.
Cheeseman, Kevin, et al. "A Diagnostic Genetic Test for the Physical Mapping of Germline Rearrangements of the Susceptibility Breast Cancer Genes BRCA1 and BRCA2." Human Mutation, vol. 33, No. 6, 998-1009, 2012.
Diggle Ma et al., A novel method for preparing single-stranded DNA for pyrosequencing, 2003, Molecular Biotechnology, 24(2):221-224.
Dong, Huimin et al. "Preparation of photodeformable azobenzene polymer fibers by post-crosslinking strategy: Understanding the structure-property relationship", European Polymer Journal, Pergamon Pressltd Oxford, GB, vol. 135, Jul. 10, 2020 (Jul. 10, 2020), XP086242455, ISSN: 0014-3057, DOI:10.1016/J.EURPOLYMJ.2020.109863.
Gad, Sophie, et al. "Identification of a large rearrangement of the BRCA1 gene using colour bar code on combed DNA in an American breast/ovarian cancer family previously studied by direct sequencing." F. Med Genet 2001, 38:388-392.
Gann et al., Development of a nuclear morphometric signature for prostate cancer risk in negative biopsies, PLoS One, Jul. 26, 2013, pp. 1-9, doi: 10.1371/journal.pone.0069457.
Guan et al., Understanding Protein Palmitoylation: Biological Significance and Enzymology, 2011, Sci China Chem. Dec. 2011; 54(12): 1888-1897 (Year: 2011).
Hamano et al., ε-Poly-L-Lysine Peptide Chain Length Regulated by the Linkers Connecting the Transmembrane Domains of £-Poly-L-Lysine Synthetase, Aug. 2014, Applied and Environmental Microbiology, vol. 80 No. 16, p. 4993-5000 (Year: 2014).
Hodson, Robert E. et al. "In Situ PCR for Visualization of Microscale Distribution of Specific Genes and Gene Products in Prokaryotic Communities." Applied and Environmental Microbiology, Nov. 1995, p. 4074-4082.
Jain, Miten et al. "Nanopore sequencing and assembly of a human genome with ultra-long reads." Nature Biotechnology, vol. 36, No. 4, Apr. 2018.
Kaykov, A., et al. "Molecular Combing of Single DNA Molecules on the 10 Megabase Scale." Sci. Rep. 6, 19636, 2016, p. 1-9.
Kleuss et al., Galphas is palmitoylated at the N-terminal glycine, The EMBO Journal vol. 22 No. 4 pp. 826-832, 2003 (Year: 2003).
Kondo, N. et al. "DNA Damage Induced by Alkylating Agents and Repair Pathways." Journal of Nucleic Acids, vol. 2010, Article ID 543531, 7 pages.
Larsson, Chatarina et al. "In situ genotyping individual DNA molecules by target-primed rolling-circle amplification of padlock probes." Nature Methods, vol. 1, No. 3, Dec. 2004.
Lunzer, Markus et al. "A Modular Approach to Sensitized Two-Photon Patterning of Photodegradable Hydrogels", Angewandte Chemie, Wiley—V CH VERLAG GmbH & Co. Kgaa, DE, vol. 130, No. 46, (Oct. 18, 2018), pp. 15342-15347, XP071375228, ISSN: 0044-8249, DOI:10.1002/ANGE.201808908.
Marie, R., et al. "Concentrating and labeling genomic DNA in a nanofluidic array." Nanoscale. 10 (2018), pp. 1376-1382.
Maxam, A. M., and Gilbert W., "A new method for sequencing DNA." Proc. Natl. Acad. Sci. U.S.A., 74, 560-564, 1977.
Nyren, Pal, et al. "Solid Phase DNA Minisequencing by an Enzymatic Luminometric Inorganic Pyrophosphate Detection Assay." Analytical Biochemistry 208, 171-175 (1993).
Rapp, Teresa L. et al. "Visible Light-Responsive Dynamic Biomaterials: Going Deeper and Triggering More", Advanced Healthcare Materials, Wiley—V CH VERLAG GmbH & Co. Kgaa, DE, vol. 9, No. 7, Feb. 25, 2020, p. n/a, XP072463096, ISSN: 2192-2640, DOI:10.1002/ADHM.201901553.
Salaun et al., The intracellular dynamic of protein palmitoylation, 2010, J. Cell Biol. vol. 191 No. 7 1229-1238 (Year: 2010).
Schirmer, M., et al. "Insight into biases and sequencing errors for amplicon sequencing with the Illumina MiSeq platform." Nucleic Acids Research, vol. 43, Issue 6, Mar. 31, 2015, e37, pp. 1-16.
Schonhuber, Wilhelm, et al. "Improved Sensitivity of Whole-Cell Hybridization by the Combination of Horseradish Peroxidase-Labeled Oligonucleotides and Tyramide Signal Amplification." Applied and Environmental Microbiology, Aug. 1997, p. 3268-3273.
Shendure, J., et al. "DNA sequencing at 40: past, present, and future." Nature Oct. 19, 2017;550(7676): 345-353.
Sikdar, Partha et al. "Recent advances in the synthesis of smart hydrogels", Materials Advances, vol. 2, No. 14, Jan. 1, 2021, pp. 4532-4573, XP093067739,DOI: 10.1039/D1MA00193K.
Singh, Anirudha et al. "Photomodulation of Cellular Gene Expression in Hydrogels", ACS Macro Letters, vol. 2, No. 3, (Mar. 8, 2013), pp. 269-272, XP093109803, ISSN: 2161-1653, DOI: 10.1021/mz300059lm.
Stankova, Helena, et al. "BioNano genome mapping of individual chromosomes supports physical mapping and sequence assembly in complex plant genomes." Plant Biotechnology Journal (2016) 14, pp. 1523-1531 doi: 10.1111/pbi.12513.
Strick, T., et al. "Twisting and stretching single DNA molecules." Progress in Biophysics & Molecular Biology 74 (2000) 115-140.
Ueda H.R., et al. "Tissue clearing and its applications in neuroscience." Nature Reviews, Neuroscience, vol. 21, Feb. 2020.
Varapula et al., A micropatterned substrate for on-surface enzymatic labelling of linearized long DNA molecules, 2019, Scientific Reports, 9, 15059.
Wages JM, Polymerase Chain Reaction, 2005, Encyclopedia of Analytical Science, (2): 243-250.
Wang et al., Detection and classification of thyroid follicular lesions based on nuclear structure from histopathology images, Cytometry A May 2010, 77(5):485-94, doi: 10.1002/cyto.a.20853. PMID: 20099247; PMCID: PMC3010854.
Wang, X., et al., "Characterization of denaturation and renaturation of DNA for DNA hybridization." Environ. Health Toxicol, 29, e2014007, 2014.
Wen et al., Specific antibody immobilization with biotin-poly(L-lysine)-g-poly(ethylene glycol) and protein A on microfluidic chips, Journal of Immunological Methods 350 (2009) 97-105 (Year: 2009).
Yanagawa, Fumiki et al. "Activated-Ester-Type Photocleavable Crosslinker for Preparation of Photodegradable Hydrogels Using a Two-Component Mixing Reaction", Advanced Healthcare Materials, Wiley—V CH VERLAG GmbH & Co. Kgaa, DE, vol. 4, No. 2, (Aug. 13, 2014), pp. 246-254, XP072465709, ISSN: 2192-2640, DOI:10.1002/ADHM.201400180.

* cited by examiner

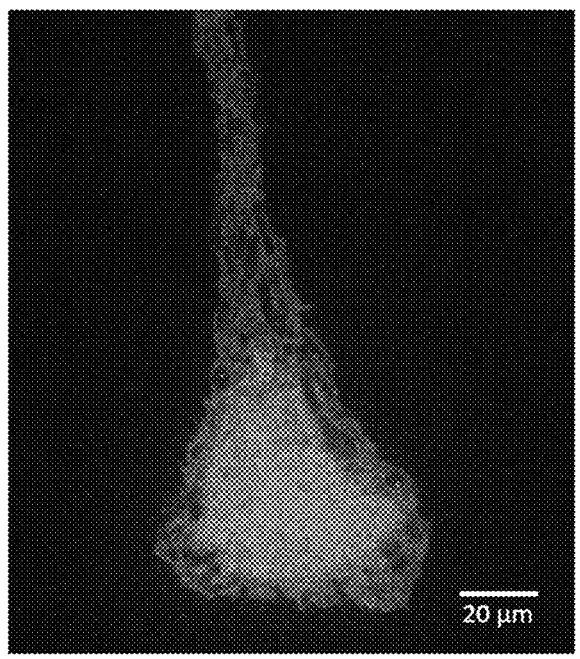
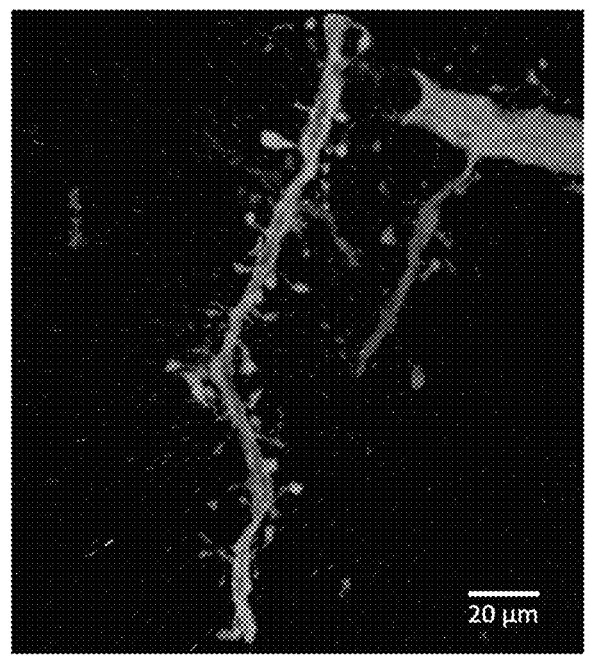
Fig. 4A                                    Fig. 4B

DIMETHYLACRYLAMIDE (DMAA) HYDROGEL FOR EXPANSION MICROSCOPY (ExM)

RELATED APPLICATION

This application is a continuation of International Application No. PCT/US2018/041930, which designated the United States and was filed on Jul. 13, 2018, published in English. The entire teachings of the above application are incorporated herein by reference.

GOVERNMENT SUPPORT

This invention was made with Government support under Grant No. NS087724 awarded by the National Institutes of Health. The Government has certain rights in the invention.

BACKGROUND OF THE INVENTION

Examination of cellular structures and molecular composition using diffraction-limited microscopy has long been key to the diagnosis of a wide variety of pre-disease and disease states. Biomolecules themselves, however, are nanoscale in dimension and configured with nanoscale precision throughout cells and tissues. In basic science, this has begun to be explored using pioneering super-resolution microscopy methods, as well as electron microscopy methods, but such strategies require complex hardware, can present a steep learning curve, and are difficult to apply to large-scale samples such as human tissues. Accordingly, super-resolution imaging and nanoscopy have not found routine utility in the clinical practice of pathology.

Thus, there is a need for higher resolution microscopy that can work with current diffraction limited microscopes and can optically magnify samples, such as tissue sections or tumors, with nanoscale precision.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4A and FIG. 4B depict high-magnification post-expansion images of pyramidal neurons in a Thy1-YFP mouse brain slice expanded by DMAA gels. (A) Post-expansion image of a pyramidal neuron soma and a segment of its apical dendrite. Scale bar: 20 μm (in post-expansion size). (B) 3D rendered post-expansion image of a pyramidal neuron dendrite segment. The ultrastructure of dendritic spines can be clearly resolved. Scale bar: 20 μm (in post-expansion size).

SUMMARY OF THE INVENTION

Figure 1A:
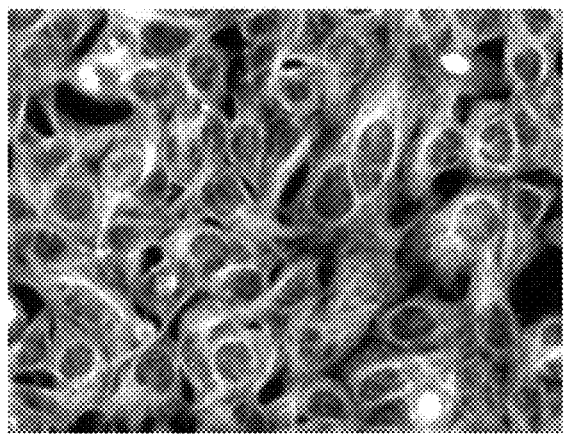
FIG. 1A and FIG. 1B depict pre-expansion (A) and post-expansion (B) images of HEK cells expanded by DMAA gels. The HEK cells were immunostained with anti-α-tubulin primary antibody and Alexa Fluor 488 secondary antibody. The expansion factor was ~6.4×.

The invention provides an expandable cell or tissue sample wherein the cell or tissue sample is embedded in a dimethylacrylamide tri-functional polymer (DMAA-TF).

The invention provides a method of preparing an expandable cell or tissue sample. The method comprises embedding the cell or tissue sample in DMAA-TF. By "preparing an expandable sample" it is generally meant that the sample is able to be physically expanded, or enlarged, relative to the sample prior to be exposed to the method(s) described herein.

In one embodiment, the method for preparing an expandable cell sample comprises the steps of incubating the sample with a composition comprising acrylamide, dimethylacrylamide, and sodium acrylate linear monomers at a concentration of about 20 about 50 wt % of which sodium acrylate comprises about 10 to about 25 mol %, about 0.1 to about 1.0 mol % polymerization initiator, and about 0.001 to about 0.01 wt % polymerization accelerator; and polymerizing the composition within the sample to form a polymer. In one embodiment, the cell sample is treated with a chemical anchoring reagent prior to incubating the sample with a composition.

In one embodiment, the method for preparing an expandable tissue sample comprises the steps of incubating the sample with a composition comprising acrylamide, dimethylacrylamide, and sodium acrylate linear monomers at a concentration of about 20 about 50 wt % of which sodium acrylate comprises about 10 to about 25 mol %, about 0.1 to about 1.0 mol % polymerization initiator, about 0.005 to about 0.02 wt % polymerization inhibitor and about 0.001 to about 0.01 wt % polymerization accelerator; and polymerizing the composition within the sample to form a polymer. In one embodiment, the tissue sample is treated with a chemical anchoring reagent prior to incubating the sample with a composition.

DETAILED DESCRIPTION

Compositions and methods are provided for imaging cell and tissue samples by physically, rather than optically, magnifying them. Briefly, biological samples are embedded in a polymer material, subjected to a treatment to disrupt native biological networks, and then expanded.

As used herein and in the appended claims, the singular forms "a", "an", and "the" are defined to mean "one or more" and include the plural unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention provides an expandable cell or tissue sample wherein the cell or tissue sample is embedded in a dimethylacrylamide tri-functional polymer (DMAA-TF).

In one embodiment, the DMAA-TF polymer (also referred to herein as "the polymer" or "swellable material") uniformly expands in 3 dimensions. Additionally, the material is transparent such that, upon expansion, light can pass through the sample. In one embodiment, the polymer is formed in situ from precursors thereof.

By "precursors of the polymer" it is meant dimethylacrylamide, acrylamide, and sodium acrylate linear monomers that can be "polymerized" through a self-crosslinking mechanism, to form a three-dimensional (3D) hydrogel network. That is free-radical polymerization of the dimethylacrylamide, acrylamide, and sodium acrylate monomers is conducted wherein the crosslinking may be attributed to competing kinetics of a polymerization initiators (e.g., potassium persulfate (KPS)) attack on dimethylacrylamide, as opposed to using a separate crosslinker such as Bis. Using a small fraction of acrylaminde linear monomer may also provide binding groups for anchoring labels (e.g., fluorescent labels) for imaging.

The precursors of the polymer may be delivered to the biological sample by any convenient method including, but not limited to, incubating, permeating, perfusing, infusing, soaking, adding or other intermixing the sample with the precursors of the polymer. In this manner, the biological sample is saturated with precursors of the polymer, which flow between and around biomolecules throughout the sample.

By embedding a sample in a DMAA-TF polymer that physically supports the ultrastructure of the sample, the biomolecules (e.g., proteins, small peptides, small molecules, and nucleic acids in the sample) are preserved in their three-dimensional distribution, secured by the polymer network. By bypassing destructive sectioning of the sample, subcellular structures may be analyzed. In addition, the sample can be iteratively stained, unstained, and restained with other reagents for comprehensive analysis.

The invention provides a method of preparing an expandable cell or tissue sample. The method comprises embedding the cell or tissue sample in DMAA-TF. By "preparing an expandable sample" it is generally meant that the sample is able to be physically expanded, or enlarged, relative to the sample prior to be exposed to the method(s) described herein.

In one embodiment, the method for preparing an expandable cell sample comprises the steps of incubating the sample with a composition comprising acrylamide, dimethylacrylamide, and sodium acrylate linear monomers at a concentration of about 20 about 50 wt % of which sodium acrylate comprises about 10 to about 25 mol %, about 0.1 to about 1.0 mol % polymerization initiator, and about 0.001 to about 0.01 wt % polymerization accelerator; and polymerizing the composition within the sample to form a polymer.

In one embodiment, the cell sample is treated with a chemical anchoring reagent prior to incubating the sample with a composition.

In one embodiment, the method for preparing an expandable tissue sample comprises the steps of incubating the sample with a composition comprising acrylamide, dimethylacrylamide, and sodium acrylate linear monomers at a concentration of about 20 about 50 wt % of which sodium acrylate comprises about 10 to about 25 mol %, about 0.1 to about 1.0 mol % polymerization initiator, about 0.005 to about 0.02 wt % polymerization inhibitor and about 0.001 to about 0.01 wt % polymerization accelerator; and polymerizing the composition within the sample to form a polymer.

In one embodiment, the tissue sample is treated with a chemical anchoring reagent prior to incubating the sample with a composition.

As used herein a chemical anchoring reagent comprises any small molecule that has both and acryloyl group and an NETS-ester group. The chemical anchoring reagent reacts with amines of biomolecules within the sample (e.g., proteins, amine-modified nucleic acids and other biomolecules) to yield acrylamides that can be copolymerized into polyacrylamide matrices. The acrylamide functional groups allow for the biomolecules to be anchored to the polymer as it is synthesized (i.e., polymerized) in situ. In embodiments, the biomolecules within the sample may be anchored to the polymer during polymerization to form a sample-polymer complex. In embodiments, the biomolecules within the sample may be anchored to the polymer after polymerization to form a sample-polymer complex.

In one embodiment, the chemical anchoring reagent comprises a protein-reactive chemical moiety and a polymer-reactive chemical moiety. The protein-reactive chemical group includes, but is not limited to, N-hydroxysuccinimide (NHS) ester, thiol, amine, maleimide, imidoester, pyridyldithiol, hydrazide, phthalimide, diazirine, aryl azide, isocyanate, or carboxylic acid, which, for example, can be reacted with amino or carboxylic acid groups on proteins or peptides. In one embodiment, the protein-reactive groups include, but are not limited to, N-succinimidyl ester, pentafluorophenyl ester, carboxylic acid, or thiol. The polymer-reactive groups include, but are not limited to, vinyl or vinyl monomers such as styrene and its derivatives (e.g., divinyl benzene), acrylamide and its derivatives, butadiene, acrylonitrile, vinyl acetate, or acrylates and acrylic acid derivatives.

Examples of such chemical crosslinking reagents include, but are not limited to, acryloyl-X, acrylic acid N-hydroxysuccinimide ester, methacrylic acid N-hydroxysuccinimide ester, acrylate-PEG-NHS.

In one embodiment, the chemical anchoring reagent that anchors proteins directly to the polymer is a succinimidyl ester of 6-((acryloyl)amino)hexanoic acid (acryloyl-X, SE; abbreviated "AcX": Life Technologies). Treatment with AcX modifies amines on proteins with an acrylamide functional group.

In embodiments, the concentration of linear monomers in the composition is about 30 to about 40 wt %. In embodiments, the concentration of linear monomers in the composition is about 35 wt %. In embodiments, the concentration of linear monomers in the composition is about 33 wt %.

In embodiments, the concentration of sodium acrylate is about 15 to about 20 mol % of the linear monomer concentration. In embodiments, the concentration of sodium acrylate is about 15 mol % of the linear monomer concentration. In embodiments, the concentration of sodium acrylate is about 20 mol % of the linear monomer concentration.

As used herein, polymerization initiator generally refers to reagents that react with a monomer to form an intermediate compound capable of linking successively with a large number of other monomers into a polymeric compound. Polymerization initiators include, but are not limited to, potassium persulfate (KPS), ammonium persulfate, di-tert-butyl peroxide (DTBP), benzoyl peroxide (BPO), methyl ethyl ketone peroxide (MEKP), acetone peroxide, VA-044 (2,2'-azobis[2-(2-imidazolin-2-yl)propane]dihydrochloride), azobisisobutyronitrile (AIBN), 1,1'-azobis(cyclohexanecarbonitrile) (ACHN), carbon halides. In embodiments, the polymerization initiator is potassium persulfate (KPS). In embodiments, the composition comprises about 0.4 mol % polymerization initiator.

As used herein, polymerization accelerator generally refers to reagents that stabilize the polymerization initiator and catalyze the polymerization process. Polymerization accelerators include, but are not limited to, N,N,N',N'-Tetramethylethylenediamine (TEMED), sodium bisulfate. In embodiments, the polymerization accelerator is TEMED. In embodiments, the composition comprises about 0.005 wt % polymerization accelerator.

As used herein, polymerization inhibitor generally refers to compounds which can trap free radicals and are used to inhibit radical polymerization. Such inhibitors may prevent polymerization initiation caused by, for example, light, heat or air. Polymerization Inhibitors include reagents that reacts very rapidly with the initiating radicals to almost completely suppress the polymerization reaction, that is, the inhibitor has to be completely consumed before the reaction rate assumes its normal value as well as reagents that react only mildy with the initiating free radicals so that some inititators escape and are able to initiate polymerizatio reduce the rate of polymerization, that is, the rate of reaction steadily increases as the retarder is consumed. The use of a polymerization inhibitor inhibits the formation of radicals allowing the composition comprising the precursors of the polymer to fully fill the cell or tissue sample. Polymerization inhibitors include, but are not limited to, 4-Hydroxy-TEMPO (4HT), 4-oxo-TEMPO, TEMPO, 4-Hydroxy-TEMPO-$d_{17}$, 4-amino-TEMPO, free radical, 4-tert-Butylcatechol, 4-tert-Butylpyrocatechol, tert-Butylhydroquinone, 1,4-Benzoquinone, 6-tert-Butyl-2,4-xylenol, 2,6-Di-tert-butyl-p-cresol, 2,6-Di-tert-butylphenol, 1,1-Diphenyl-2-picrylhydrazyl Free Radical, Hydroquinone, 4-Methoxyphenol, Phenothiazine. In embodiments, the polymerization inhibitor is 4HT. In embodiments, the composition comprises about 0.01 wt % polymerization inhibitor.

After the sample has been anchored to the polymer, the sample may be subjected to digestion. As used herein, "digestion" generally refers to the disruption of the endogenous biological molecules (or the physical structure of the biological sample), leaving the macromolecules, e.g., label or tag, that preserve the information of the biomolecules intact and anchored to the polymer. In this way, the mechanical properties of the sample-polymer complex are rendered more spatially uniform, allowing greater and more consistent isotropic expansion.

The disruption of the endogenous physical structure of the sample or of the endogenous biomolecules of the sample generally refers to the mechanical, physical, chemical, biochemical or, enzymatic digestion, disruption or break up of the sample so that it will not resist expansion. In one embodiment, a non-specific protease is used to homogenize the sample-polymer complex. In one embodiment, the method may further comprise the step of incubating the sample with a non-specific protease in a buffer comprising a metal ion chelator, a non-ionic surfactant, and a monovalent salt. In one embodiment, the method comprises incubating the sample with 1-100 U/ml of a non-specific protease in a buffer having a pH between about 4 and about 12, the buffer comprising about 5 mM to about 100 mM metal ion chelator, about 0.1% to about 1.0% non-ionic surfactant, and about 0.05 M to about 1 M monovalent salt. In one embodiment, the sample is incubated for about 0.5 to about 3 hours at about 50° C. to about 70° C. In one embodiment, the sample is incubated in the buffer until the sample is completely digested.

In one embodiment, the non-specific protease is in a buffer having a pH from about 4 to about 12. Any suitable buffer agent can be used including, but not limited to, Tris, citrate, phosphate, bicarbonate, MOPS, borate, TAPS, bicine, Tricine, HEPES, TES, and MES.

Non-specific proteases are well known to those of skill in the art. Non-specific proteases include, but are not limited to, proteinase K, Subtilisin, Pepsin, Thermolysin, and Elastase. In one embodiment the buffer comprises about 1 U/ml to about 100 U/ml of a non-specific protease. In one embodiment the buffer comprises about 1 U/ml to about 50 U/ml of a non-specific protease. In one embodiment the buffer comprises about 1 U/ml to about 25 U/ml of a non-specific protease. In one embodiment the buffer comprises about 1 U/ml to about 10 U/ml of a non-specific protease.

Chelating agents are well known to those of skill in the art. Chelating agents include, but are not limited to, EDTA, EGTA, EDDHA, EDDS, BAPTA and DOTA. In one embodiment the buffer comprises about 5 mM to about 100 mM of a metal ion chelator. In one embodiment the buffer comprises about 5 mM to about 75 mM of a metal ion chelator. In one embodiment the buffer comprises about 5 mM to about 50 mM of a metal ion chelator.

Nonionic surfactant are well known to those of skill in the art. Nonionic surfactants include, but are not limited to, Triton X-100, Tween 20, Tween 80, Sorbitan, Polysorbate 20, Polysorbate 80, PEG, Decyl glucoside, Decyl polyglucose and cocamide DEA. In one embodiment the buffer comprises about 0.1% to about 1.0% nonionic surfactant. In one embodiment the buffer comprises about 0.1% to about 0.75% nonionic surfactant. In one embodiment the buffer comprises about 0.1% to about 0.5% nonionic surfactant. In one embodiment the buffer comprises about 0.1% to about 0.3% nonionic surfactant.

Monovalent cation salts are well known to those of skill in the art. Monovalent cation salts contain cations that include, but are not limited to, $Na^+$, $K^+$, ammonium, and $Cs^+$. In one embodiment, the buffer comprises about 0.05 M to about 1.0 M monovalent salt. In one embodiment, the buffer comprises about 0.05 M to about 1.0 M monovalent salt. In one embodiment, the buffer comprises about 0.75 M to about 1.0 M monovalent salt. In one embodiment, the buffer comprises about 0.1 M to about 1.0 M monovalent salt. In one embodiment, the buffer comprises about 0.1 M to about 0.7 M monovalent salt. In one embodiment, the buffer comprises about 0.05 M to about 0.8 M monovalent salt.

It is preferable that the disruption does not impact the structure of the polymer but disrupts the structure of the sample. Thus, the sample disruption should be substantially inert to the polymer. The degree of digestion can be sufficient to compromise the integrity of the mechanical structure of the sample or it can be complete to the extent that the sample-polymer complex is rendered substantially free of the sample.

The expandable cell or tissue sample can be expanded by contacting the sample-polymer complex with a solvent or liquid to cause the polymer to swell. By expanding, or swelling, the expandable sample it is generally meant that the sample is physically expanded, or enlarged, relative to the sample prior to be exposed to the method(s) described herein. The swelling of the polymer results in the sample itself expanding (e.g., becoming larger). This is because the polymer is embedded throughout the sample, therefore, by binding, e.g., anchoring, biomolecules to the polymer network and swelling, or expanding, the polymer network, the biomolecules are thereby moved apart. In one embodiment, the swellable polymer expands (swells) isotropically. As the biomolecules are anchored to the polymer network isotropic expansion of the polymer network retains the spatial orientation of the biomolecules resulting in an expanded, or enlarged, sample.

The expanded sample can then be subjected to microscopic analysis. By "microscopic analysis" it is meant the analysis of a sample using any technique that provides for the visualization of aspects of a sample that cannot be seen with the unaided eye, i.e., that are not within the resolution range of the normal eye.

The expanded sample-polymer complex can be imaged on any optical microscope, allowing effective imaging of features below the classical diffraction limit. Since the resultant expanded sample can be transparent, custom microscopes capable of large volume, wide field of view, 3D scanning may also be used in conjunction with the expanded sample.

Because biomolecules of the sample are anchored to a polymer that physically supports the ultrastructure of the sample, cellular components (e.g., lipids) that normally provide structural support but that hinder visualization of subcellular proteins and molecules may be removed while preserving the 3-dimensional architecture of the cells and tissue. This removal renders the interior of sample substantially permeable to light and/or macromolecules, allowing the interior of the sample, e.g., cells and subcellular structures, to be microscopically visualized without time-consuming and disruptive sectioning.

Additionally, the sample can be iteratively stained, unstained, and re-stained with other reagents for comprehensive analysis.

The term "tissue sample" is used herein in a broad sense and is intended to include sources that contain biomolecules and can be fixed. Exemplary tissue samples include, but are not limited to liver, spleen, kidney, lung, intestine, thymus, colon, tonsil, testis, skin, brain, heart, muscle and pancreas tissue. Other exemplary tissue samples include, but are not limited to, biopsies, bone marrow samples, organ samples, skin fragments and organisms. Materials obtained from clinical or forensic settings are also within the intended meaning of the term tissue sample. In one embodiment, the sample is derived from a human, animal or plant. In one embodiment, samples are human. The sample can be obtained, for example, from autopsy, biopsy or from surgery. It can be a solid tissue such as, for example, parenchyme, connective or fatty tissue, heart or skeletal muscle, smooth muscle, skin, brain, nerve, kidney, liver, spleen, breast, carcinoma (e.g., bowel, nasopharynx, breast, lung, stomach etc.), cartilage, lymphoma, meningioma, placenta, prostate, thymus, tonsil, umbilical cord or uterus. The tissue can be a tumor (benign or malignant), cancerous or precancerous tissue. The sample can be obtained from an animal or human subject affected by disease or other pathology or suspected of same (normal or diseased) or considered normal or healthy. As used herein, the term "tissue sample" explicitly excludes cell-free samples, for example cell extracts, wherein cytoplasmic and/or nuclear components from cells are isolated.

Tissue samples suitable for use with the methods and systems described herein generally include any type of tissue samples collected from living or dead subjects, such as, e.g., biopsy specimens and autopsy specimens. Tissue samples may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue samples in a stable, accessible and fully intact form for future analysis. For example, tissue samples, such as, e.g., human brain tissue samples, may be processed as described above and cleared to remove a plurality of cellular components, such as, e.g., lipids, and then stored for future analysis.

Tissues that have been preserved, or fixed, contain a variety of chemical modifications that can reduce the detectability of proteins in biomedical procedures. In some embodiments, the methods and systems described herein may be used to analyze a previously-preserved or stored tissue sample. Previously preserved tissue samples include, for example, clinical samples used in pathology including formalin-fixed paraffin-embedded (FFPE), hematoxylin and eosin (H&E)-stained, and/or fresh frozen tissue samples. If the previously preserved sample has a coverslip, the coverslip should be removed. The sample is treated to remove the mounting medium. Such methods for removing the mounting medium are well known in the art. For example, treating the sample with xylene to remove paraffin or other hydrophobic mounting medium.

Alternatively, if the sample is mounted in a water-based mounting medium, the sample is treated with water. The sample is then then rehydrated and subjected to antigen-retrieval. The term "antigen retrieval" refers to any technique in which the masking of an epitope is reversed and epitope-antibody binding is restored such as, but not limited to, enzyme induced epitope retrieval, heat induced epitope retrieval (HIER), or proteolytic induced epitope retrieval (PIER). For example, the antigen retrieval treatment can be performed in a 10 mM sodium citrate buffer as well as the commercially available Target Retrieval Solution (DakoCytomation) or such.

By "biomolecules" it is generally meant, but not limited to, proteins, lipids, steroids, nucleic acids, and sub-cellular structures within a tissue or cell.

By "macromolecules" is meant proteins, nucleic acids, or small molecules that target biomolecules within the sample. These macromolecules are used to detect biomolecules within the sample and/or anchor the biolmolecules to the swellable polymer. For example, macromolecules may be provided that promote the visualization of particular cellular biomolecules, e.g., proteins, lipids, steroids, nucleic acids, etc. and sub-cellular structures. In some embodiments, the macromolecules are diagnostic. In some embodiments, the macromolecules are prognostic. In some embodiments, the macromolecules are predictive of responsiveness to a therapy. In some embodiments, the macromolecules are candidate agents in a screen, e.g., a screen for agents that will aid in the diagnosis and/or prognosis of disease, in the treatment of a disease, and the like.

As an example, the sample may be contacted with one or more polypeptide macromolecules, e.g. antibodies, labeled peptides, and the like, that are specific for and will bind to particular cellular biomolecules for either direct or indirect labeling by color or immunofluorescence. By immunofluorescence it is meant a technique that uses the highly specific binding of an antibody to its antigen or binding partner in order to label specific proteins or other molecules within the cell. A sample is treated with a primary antibody specific for the biomolecule of interest. A fluorophore can be directly conjugated to the primary antibody or peptide. Alternatively a secondary antibody, conjugated to a detection moiety or fluorophore, which binds specifically to the first antibody can be used. Peptides that are specific for a target cellular biomolecule and that are conjugated to a fluorophore or other detection moiety may also be employed.

Another example of a class of agents that may be provided as macromolecules is nucleic acids. For example, a sample may be contacted with an antisense RNA that is complementary to and specifically hybridizes to a transcript of a gene of interest, e.g., to study gene expression in cells of the sample. As another example, a sample may be contacted with a DNA that is complementary to and specifically hybridizes to genomic material of interest, e.g., to study genetic mutations, e.g., loss of heterozygosity, gene duplication, chromosomal inversions, and the like. The hybridizing RNA or DNA is conjugated to detection moieties, i.e., agents that may be either directly or indirectly visualized microscopically. Examples of in situ hybridization techniques may be found at, for example, Harris and Wilkinson. In situ hybridization: Application to developmental biology and medicine, Cambridge University Press 1990; and Fluorescence In Situ Hybridization (FISH) Application Guide. Liehr, T, ed., Springer-Verlag, Berlin Heidelberg 1990.

In one embodiment, the cell or tissue sample can be labeled or tagged with a detectable label. Typically, the label or tag will bind chemically (e.g., covalently, hydrogen bonding or ionic bonding) to a biomolecule of the sample, or a component thereof. The detectable label can be selective for a specific target (e.g., a biomarker or class of molecule), as can be accomplished with an antibody or other target specific binder. The detectable label may comprise a visible component, as is typical of a dye or fluorescent molecule; however any signaling means used by the label is also contemplated. A fluorescently labeled biological sample, for example, is a biological sample labeled through techniques such as, but not limited to, immunofluorescence, immuno-histochemical or immunocytochemical staining to assist in microscopic analysis. In one embodiment, the detectable label is chemically attached to the biological sample, or a targeted component thereof. In one embodiment, the detectable label is an antibody and/or fluorescent dye wherein the antibody and/or fluorescent dye, further comprises a physical, biological, or chemical anchor or moiety that attaches or crosslinks the cell or tissue sample to the polymer. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample.

In one embodiment, the proteins of the sample of interest can be modified with the protein-reactive group and the gel-reactive group in separate steps using click chemistry. Click chemistry, also referred to as tagging, is a class of biocompatible reactions intended primarily to join substrates of choice with specific biomolecules. In this method, proteins of the sample of interest are treated with a protein-reactive group comprising a click group and then treated with a gel-reactive group comprising a complementary click group. Complementary groups include, but are not limited to, azide groups and terminal alkynes (see e.g., H. C. Kolb; M. G. Finn; K B. *Sharpless* (2001). *"Click Chemistry: Diverse Chemical Function from a Few Good Reactions". Angewandie Chemie International Edition.* 40(11): 2004-2021, which is incorporated herein by reference).

In some embodiments, native proteins anchored to the polymer perfused throughout the sample as described herein can retain epitope functionality and can be labeled post-expansion. Such approaches may overcome the limitations inherent to delivering antibodies in the crowded environment of native tissue.

In some embodiments, the enlarged sample can be re-embedded in a non-swellable polymer. "Re-embedding" comprises permeating (such as, perfusing, incubating, infusing, soaking, adding or other intermixing) the sample with the non-swellable polymer, preferably by adding precursors thereof. Alternatively or additionally, embedding the sample in a non-swellable polymer comprises permeating one or more monomers or other precursors throughout the sample and polymerizing and/or crosslinking the monomers or precursors to form the non-swellable polymer or polymer. In this manner the first enlarged sample, for example, is embedded in the non-swellable polymer. Embedding the expanded sample in a non-swellable polymer prevents conformational changes during sequencing despite salt concentration variation. The non-swellable polymer can be charge-neutral hydrogels. For example, it can be polyacrylamide hydrogel, composed of acrylamide monomers, bisacrylamide crosslinker, ammonium persulfate (APS) initiator and tetramethylethylenediamine (TEMED) accelerator.

In some embodiments, the fixed biological sample is subjected to passivation. As used herein the term "passivation" refers to the process for rendering the sample less reactive with the components contained within the fixative such as by functionalizing the fixative with chemical reagents to neutralize charges within. For example, the carboxylic groups of acrylate, which may be used in the swellable gel, can inhibit downstream enzymatic reactions. Treating the swellable gel composed of acrylate with 1-Ethyl-3-(3-dimethylaminopropyl)carbodiimide (EDC) and N-Hydroxysuccinimide (NETS) allows primary amines to covalently bind the carboxylic groups to form charge neutral amides and passivate the swellable gel.

The innovation enables physical expansion of common clinical tissue sample based on the unique physical and chemical properties of clinical tissue samples. Clinical tissue samples are usually highly fixed, tightly attached on the superfrost glass slides, and embedded in the paraffin (or stained and mounted in a mounting medium) for long-term storage. Some clinical tissue samples are stained with dyes, such as hematoxylin and eosin (H&E), which are incompatible with fluorescence imaging. To apply ExM to clinical samples, de-paraffinization, antigen retrieval and aggressive protease digestion are integrated in a comprehensive workflow to handle various kinds of common clinical samples. De-paraffinization and antigen retrieval address the recovery of archived clinical samples, while aggressive protease digestion is critical for the success of sample expansion, as most of the human tissues contain abundant hard-to-digest structural proteins, such as collagen and fibronectin, which prevent homogeneous expansion of the sample. Taken together, the present invention allows for the application of ExM to the enormous amount of archived clinical samples and enable super-resolution optical interrogations of mechanisms of a broad range of diseases by conventional optical microscopy.

This invention provides a comprehensive workflow to facilitate expansion of common types of clinical samples for super-resolution molecular imaging. The methods described herein will result in optimal outcomes, such as proper immunostaining, sufficient digestion of tissue, high quality of polymer synthesis, and maintenance of proteins of interest during expansion.

The invention also describes the reutilization of classic H&E stained slides for further biomolecular interrogation in nanoscale level. In general, H&E stained slides are not considered suitable for further downstream processing due to the difficulty in removing the stain and mounting medium. Thus, the invention describes a unique and cost-effective approach to overcome this barrier and enable the extraction of more information from the used H&E slides. In one embodiment, the method of expanding H&E stained slides for further utilization combines xylene-ethanol-water sequential washing, protein anchoring and in situ polymer synthesis.

The subject methods find many uses. For example, the subject methods may be applied to preparing specimens for the study of the connectivity of the central nervous system. "Connectivity" as used herein generally means the connections between neurons, and includes connections at the single cell level, e.g., synapses, axon termini, dendritic spines, etc., as well as connections between groups of neurons and regions of the CNS as major axon tracts, e.g., corpus callosum (CC), anterior commissure (AC), hippocampal commissure (HC), pyramidal decussation, pyramidal tracts, external capsule, internal capsule (IC), cerebral peduncle (CP), etc. A whole brain and/or spinal cord specimen or region thereof (e.g. cerebrum (i.e., cerebral cortex), cerebellum (i.e., cerebellar cortex), ventral region of the forebrain (e.g., striatum, caudate, putamen, globus pallidus, nucleus accumbens; septal nuclei, subthalamic nucleus); regions and nuclei of the thalamus and hypothalamus; regions and nuclei of the deep cerebellum (e.g., dentate nucleus, globose nucleus, emboliform nucleus, fastigial nucleus) and brainstem (e.g., substantia nigra, red nucleus, pons, olivary nuclei, cranial nerve nuclei); and regions of the spine (e.g., anterior horn, lateral horn, posterior horn)) may be prepared post-mortem by the subject methods and the connectivity of the neurons therein microscopically analyzed, e.g., obtained, stored, rendered, used, and actuated, e.g., to provide the full connectivity of a brain, e.g., a human brain, after death. Such studies will contribute greatly to the understanding of how the brain develops and functions in health and during disease, and of the underpinnings of cognition and personality.

As another example, the subject methods may be employed to evaluate, diagnose or monitor a disease. "Diagnosis" as used herein generally includes a prediction of a subject's susceptibility to a disease or disorder, determination as to whether a subject is presently affected by a disease or disorder, prognosis of a subject affected by a disease or disorder (e.g., identification of cancerous states, stages of cancer, likelihood that a patient will die from the cancer), prediction of a subject's responsiveness to treatment for a disease or disorder (e.g., a positive response, a negative response, no response at all to, e.g., allogeneic hematopoietic stem cell transplantation, chemotherapy, radiation therapy, antibody therapy, small molecule compound therapy) and use of therametrics (e.g., monitoring a subject's condition to provide information as to the effect or efficacy of therapy). For example, a biopsy may be prepared from a cancerous tissue and microscopically analyzed to determine the type of cancer, the extent to which the cancer has developed, whether the cancer will be responsive to therapeutic intervention, etc.

As another example, a biopsy may be prepared from a diseased tissue, e.g., kidney, pancreas, stomach, etc., to determine the condition of the tissue, the extent to which the disease has developed, the likelihood that a treatment will be successful, etc. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans. Examples of diseases that are suitable to evaluation, analysis, diagnosis, prognosis, and/or treatment using the subject methods and systems include, but are not limited to, cancer, immune system disorders, neuropsychiatric disease, endocrine/reproductive disease, cardiovascular/pulmonary disease, musculoskeletal disease, gastrointestinal disease, and the like.

The subject methods may also be used to evaluate normal tissues, organs and cells, for example to evaluate the relationships between cells and tissues of a normal tissue sample, e.g., a tissue sample taken from a subject not known to suffer from a specific disease or condition. The subject methods may be used to investigate, e.g., relationships between cells and tissues during fetal development, such as, e.g., during development and maturation of the nervous system, as well as to investigate the relationships between cells and tissues after development has been completed, e.g., the relationships between cells and tissues of the nervous systems of a fully developed adult sample.

The subject methods also provide a useful system for screening candidate therapeutic agents for their effect on a tissue or a disease. For example, a subject, e.g., a mouse, rat, dog, primate, human, etc. may be contacted with a candidate agent, an organ or a biopsy thereof may be prepared by the subject methods, and the prepared sample microscopically analyzed for one or more cellular or tissue parameters. Parameters are quantifiable components of cells or tissues, particularly components that can be accurately measured, desirably in a high throughput system.

The subject methods may also be used to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, ancestry, and the like. Such detection may be used in, for example, diagnosing and monitoring disease as, e.g., described above, in personalized medicine, and in studying paternity.

EXAMPLES

Preparing Expandable Cell Samples

Cell samples were fixed and pretreated with 0.1 mg/mL acryloyl-X solution in 1×PBS overnight and washed with 1×PBS immediately before gelation. A solution consisting of 33 wt % total monomers (of which sodium acrylate constituted 15-20 mol %) was prepared as follows. For 15 mol %, a total of 180 uL sodium acrylate (387 mg/mL), 432 uL DMAA, and 718 uL $H_2O$ were mixed; for 20 mol %, a total of 240 uL sodium acrylate (387 mg/mL), 407 uL DMAA, and 669 uL $H_2O$ were mixed. The solution was centrifuged for 2 min at 4700 xg to remove turbidity. The top layer was then separated from the smaller bottom layer, which was discarded. The remaining solution (top layer) was bubbled with dry nitrogen for 30-45 min. Potassium persulfate (KPS, stock solution: 42 mg/mL in $H_2O$) was then added to a final concentration of 0.4 mol %, followed by an additional ~15 min of bubbling with dry nitrogen. To this solution was added 6.2 μL TEMED to yield the gelling solution, in which the cell samples (which was optionally pre-incubated with monomer solution prior to KPS addition for ~10 min) were immediately incubated. The samples were stored in a humidified chamber at room temperature or 4° C. for approximately 24 h to allow for complete gelation.

After proteinase K treatment (8 units/mL in digestion buffer) overnight, the gelled samples were expanded in double-distilled water 3×20 min. We note the nitrogen bubbling step is optional as long as the concentration of oxygen species is kept low in the gelling solution and during the gelling process.

Preparing Expandable Tissue Samples

Tissue samples were fixed and pretreated with 0.1 mg/mL acryloyl-X solution in 1×PBS overnight and washed with 1×PBS immediately before gelation. The gelling solution was prepared following the above protocol with a slight modification. In addition to KPS and TEMED, 4-Hydroxy-TEMPO (4HT) (stock solution: 0.5 wt %) was added to a final concentration of 0.01 wt % to yield the gelling solution. This is to allow the gelling solution to diffuse through the tissue sample for a longer time before the gelation starts. Tissue samples were incubated in the gelling solution and then stored in a humidified chamber at 4° C. for approximately 24 h to allow for complete gelation.

After proteinase K treatment (8 units/mL in digestion buffer) overnight, the gelled samples were expanded in double-distilled water 3×20 min.

Pre-Expansion and Post-Expansion Images of HEK Cells Expanded by DMAA Gels

Figure 1B:
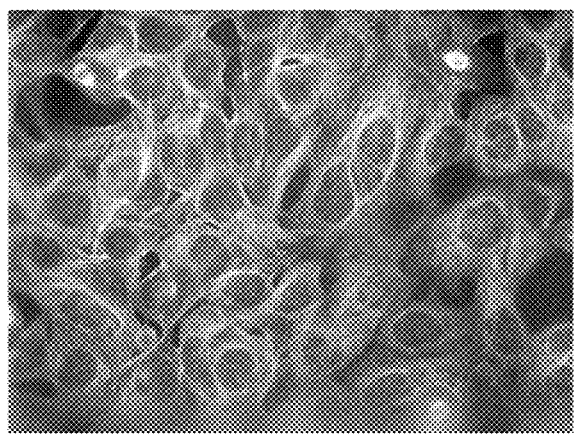
Figures 2A, 2B:
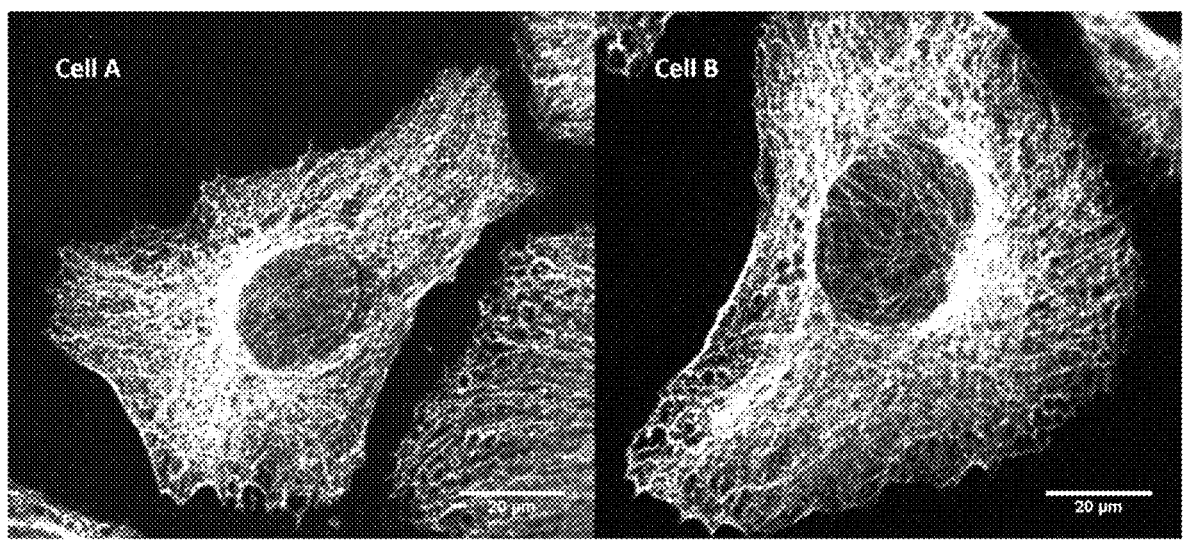
FIG. 2A and FIG. 2B depict high magnification post-expansion images of HEK cells expanded by DMAA gels. The HEK cells were immunostained with anti-α-tubulin primary antibody and Alexa Fluor 488 secondary antibody. Scale bars: 20 μm (in post-expansion size).

HEK cells were immunostained with anti-α-tubulin primary antibody and Alexa Fluor 488 secondary antibody and then embedded in a DMAA hydrogel as described above. The HEK cell/DMAA hydrogel composites were expanded in water 3×20 min and subjected to microscopic analysis. The results are shown in FIG. 1. High magnification post-expansion images of the HEK cells are shown in FIG. 2.

Figure 3A:
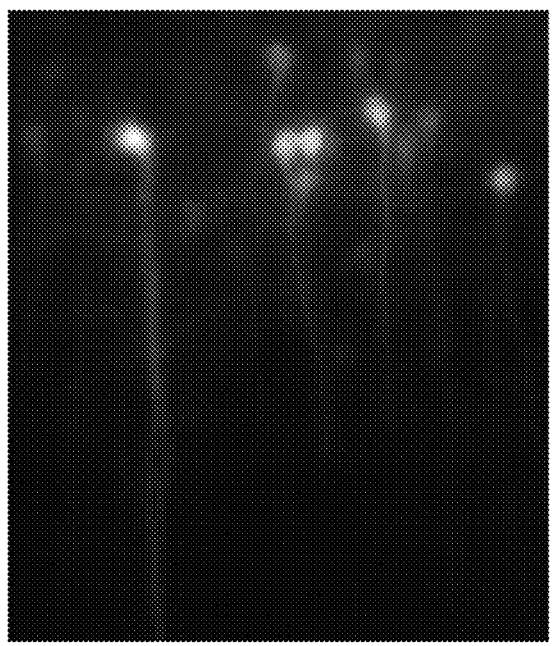
FIG. 3A and FIG. 3B depict pre-expansion (A) and post-expansion (B) images of pyramidal neurons in a Thy1-YFP mouse brain slice expanded by DMAA gels. The pre-expansion and post-expansion images were captured with a 20× and 4× objective, respectively. The expansion factor was ~8.1×.
Figure 3B:

Pre-Expansion and Post-Expansion Images of Pyramidal Neurons in a Thy1-YFP Mouse Brain expanded by DMAA gels Tissue from Thy1-YFP mouse brain were embedded in a DMAA hydrogel as described above. The mouse brain/DMAA hydrogel composites were expanded in water 3×20 min and subjected to microscopic analysis. The results are shown in FIG. 3. High-magnification post-expansion images of pyramidal neurons in a Thy1-YFP mouse brain are shown in FIG. 4.

While this invention has been particularly shown and described with references to preferred embodiments thereof, it will be understood by those skilled in the art that various changes in form and details may be made therein without departing from the scope of the invention encompassed by the appended claims.

What is claimed:

1. A method for preparing an expandable tissue sample, the method comprising the steps of:
   (a) incubating a tissue sample with a composition comprising:
      precursors of a polymer, the precursors comprising linear monomers at a concentration of about 20 to about 50 wt %, wherein the linear monomers comprise acrylamide, dimethylacrylamide, and sodium acrylate, and wherein the sodium acrylate is about 10 to about 25 mol % of the linear monomers,
      about 0.1 to about 1.0 mol % polymerization initiator,
      about 0.005 to about 0.02 wt % polymerization inhibitor, and
      about 0.001 to about 0.01 wt % polymerization accelerator,
      wherein the composition does not include a separate crosslinker from the dimethylacrylamide; and
   (b) polymerizing the composition within the tissue sample to form a polymer, wherein the polymer is embedded throughout the tissue sample.

2. The method according to claim 1, further comprising, prior to incubating the tissue sample with the composition, treating the tissue sample with a chemical anchoring reagent.

3. The method according to claim 2, wherein the chemical anchoring reagent is acryloyl-X.

4. The method according to claim 2, wherein the polymerizing results in covalent anchoring of biomolecules within the tissue sample to the polymer to form a sample-polymer complex.

5. The method according to claim 4, wherein the biomolecules within the tissue sample are anchored to the polymer during and/or after the polymerization.

6. The method according to claim 1, wherein the concentration of the linear monomers in the composition is about 30 to about 40 wt %.

7. The method according to claim 6, wherein the concentration of the linear monomers in the composition is about 35 wt %.

8. The method according to claim 6, wherein the concentration of the linear monomers in the composition is about 33 wt %.

9. The method according to claim 1, wherein the sodium acrylate is about 15 to about 20 mol % of the linear monomers.

10. The method according to claim 9, wherein the sodium acrylate is about 15 mol % of the linear monomers.

11. The method according to claim 9, wherein the sodium acrylate is about 20 mol % of the linear monomers.

12. The method according to claim 1, wherein the composition comprises about 0.4 mol % polymerization initiator.

13. The method according to claim 1, wherein the polymerization initiator is potassium persulfate (KPS).

14. The method according to claim 1, wherein the composition comprises about 0.005 wt % polymerization accelerator.

15. The method according to claim 1, wherein the polymerization accelerator is N,N,N',N'-Tetramethylethylenediamine (TEMED).

16. The method according to claim 1, wherein the composition comprises about 0.01 wt % polymerization inhibitor.

17. The method according to claim 1, wherein the polymerization inhibitor is 4-Hydroxy-TEMPO.

18. The method according to claim 1, further comprising, prior to performing the incubating, treating the tissue sample with a detergent.

19. The method according to claim 1, wherein the polymerizing results in formation of a tissue sample-polymer complex, and wherein the method further comprises adding an aqueous solvent or liquid to cause the polymer to swell, thereby physically expanding the tissue sample-polymer complex and forming an expanded tissue sample-polymer complex.

20. The method according to claim 19, wherein the tissue sample-polymer complex expands isotropically.

21. The method according to claim 19, wherein the aqueous solvent or liquid is water.

22. The method according to claim 19, further comprising, prior to adding the aqueous solvent or liquid to swell the polymer, subjecting the tissue sample-polymer complex to digestion.

23. The method according to claim 22, wherein the digestion comprises incubating the tissue sample-polymer complex with a composition comprising a non-specific protease.

24. The method according to claim 23, wherein the composition comprises the non-specific protease in a buffer comprising a metal ion chelator, a non-ionic surfactant, and a monovalent salt.

25. The method according to claim 24, wherein the composition comprises about 1 to about 100 U/ml of the non-specific protease in the buffer having a pH between about 4 and about 12, the buffer comprising about 5 mM to about 100 mM of the metal ion chelator, about 0.1% to about 1.0% of the non-ionic surfactant, and about 0.05 M to about 1.0 M of the monovalent salt, for about 0.5 to about 3 hours at about 50° C. to about 70° C.

26. The method according to claim 19, further comprising producing a high-resolution image of the tissue sample by viewing the expanded tissue sample-polymer complex under a microscope.

27. The method according to claim 19, further comprising optically imaging the tissue sample by viewing the expanded tissue sample-polymer complex under a microscope.

28. A method for preparing an expandable cell sample, the method comprising the steps of:
(a) incubating a cell sample with a composition comprising:
precursors of a polymer, the precursors comprising linear monomers at a concentration of about 20 to about 50 wt %, wherein the linear monomers comprise acrylamide, dimethylacrylamide, and sodium acrylate, and wherein the sodium acrylate is about 10 to about 25 mol % of the linear monomers,
about 0.1 to about 1.0 mol % polymerization initiator, and
about 0.001 to about 0.01 wt % polymerization accelerator,
wherein the composition does not include a separate crosslinker from the dimethylacrylamide; and
(b) polymerizing the composition within the cell sample to form a polymer, wherein the polymer is embedded throughout the cell sample.

* * * * *

UNITED STATES PATENT AND TRADEMARK OFFICE
CERTIFICATE OF CORRECTION

PATENT NO. : 12,233,184 B2
APPLICATION NO. : 17/144551
DATED : February 25, 2025
INVENTOR(S) : Boyden et al.

It is certified that error appears in the above-identified patent and that said Letters Patent is hereby corrected as shown below:

In the Specification

In Column 1, Lines 11-13, delete:
"This invention was made with Government support under Grant No. NS087724 awarded by the National Institutes of Health. The Government has certain rights in the invention."

And insert:
-- This invention was made with government support under NS087724, R01 EB024261, and U01 MH114819 awarded by the National Institutes of Health, and W911NF-15-1-0548 awarded by the U.S. Army Research Office. The government has certain rights in the invention. --

Signed and Sealed this
Eleventh Day of November, 2025

John A. Squires
*Director of the United States Patent and Trademark Office*